United States Patent [19]
Hayakawa

[11] Patent Number: 6,146,329
[45] Date of Patent: Nov. 14, 2000

[54] ULTRASONIC DIAGNOSTIC APPARATUS

[75] Inventor: Kenichi Hayakawa, Kawasaki, Japan

[73] Assignee: Fujitsu Limited, Kawasaki, Japan

[21] Appl. No.: 09/257,496

[22] Filed: Feb. 25, 1999

Related U.S. Application Data

[62] Division of application No. 08/974,517, Nov. 19, 1997.

[30] Foreign Application Priority Data

Jul. 15, 1997  [JP]  Japan .................................... 9-190082

[51] Int. Cl.$^7$ ...................................................... A61B 8/00
[52] U.S. Cl. ........................................... 600/443; 600/461
[58] Field of Search ................................... 600/440, 443, 600/447, 459, 461, 464, 471

[56] References Cited

U.S. PATENT DOCUMENTS

| | | |
|---|---|---|
| 4,249,539 | 2/1981 | Vilkomerson et al. . |
| 4,346,717 | 8/1982 | Haerten . |
| 4,567,896 | 2/1986 | Barrea et al. ............................ 600/461 |
| 4,870,867 | 10/1989 | Shaulov ................................... 73/625 |
| 5,095,910 | 3/1992 | Powers . |
| 5,318,033 | 6/1994 | Savord . |
| 5,379,642 | 1/1995 | Reckwerdt et al. ....................... 73/625 |
| 5,471,989 | 12/1995 | Roundhill et al. ...................... 600/440 |
| 5,967,895 | 10/1999 | Hayakawa et al. ..................... 600/440 |

FOREIGN PATENT DOCUMENTS

| | | |
|---|---|---|
| 33 11 804 | 10/1984 | Germany . |
| 36 17 235 | 11/1987 | Germany . |
| 63-290550 | 11/1988 | Japan . |

OTHER PUBLICATIONS

Abstract of Japan, Ultrasonic Tomographic Apparatus for Guiding Puncture Needle, Nov. 28, 1988, Hitachi Medical Corp, Kenichi Hirayae.

*Primary Examiner*—Francis J. Jaworski
*Attorney, Agent, or Firm*—Staas & Halsey LLP

[57] ABSTRACT

There is provided an ultrasonic diagnostic apparatus in which ultrasonic waves are transmitted into the subject, the ultrasonic waves reflected within the subject are received to obtain received signals, and an image is produced in accordance with the received signals thus obtained, and particularly to an ultrasonic diagnostic apparatus having a function of guiding a puncture needle to be introduced into the subject. Of a scanning area formed with a number of scanning lines scanned by ultrasonic waves, within the subject, a first area including a part or a whole of a passage of a puncture needle is scanned with a scanning density higher than that of a second area, excepting the first area, of said scanning area. A sensor which measures the tip length of the puncture needle is used to set up the first area.

12 Claims, 16 Drawing Sheets

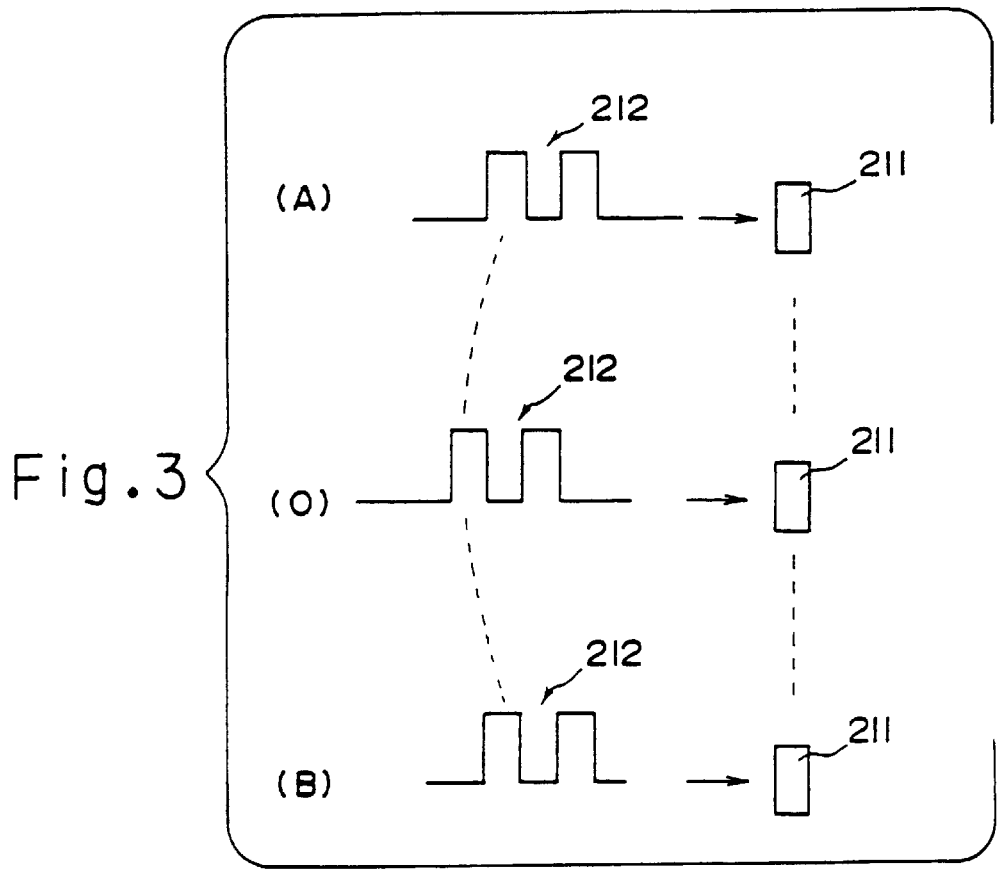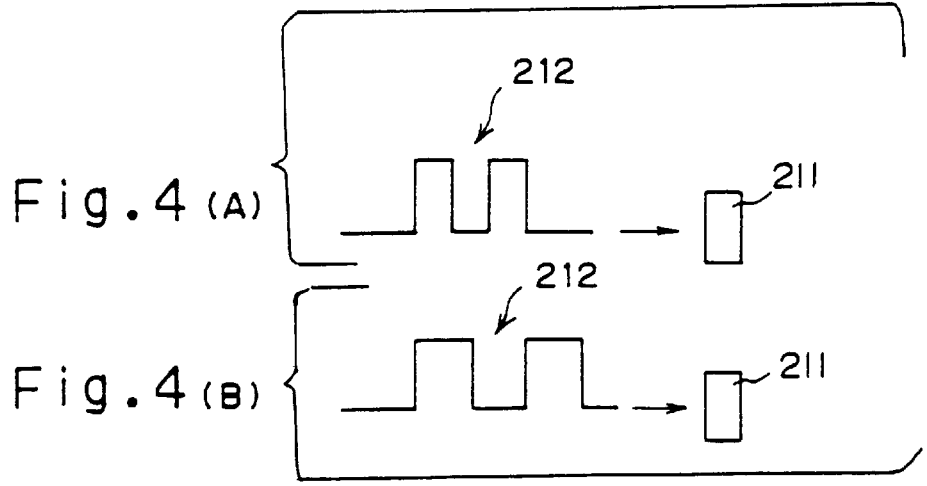

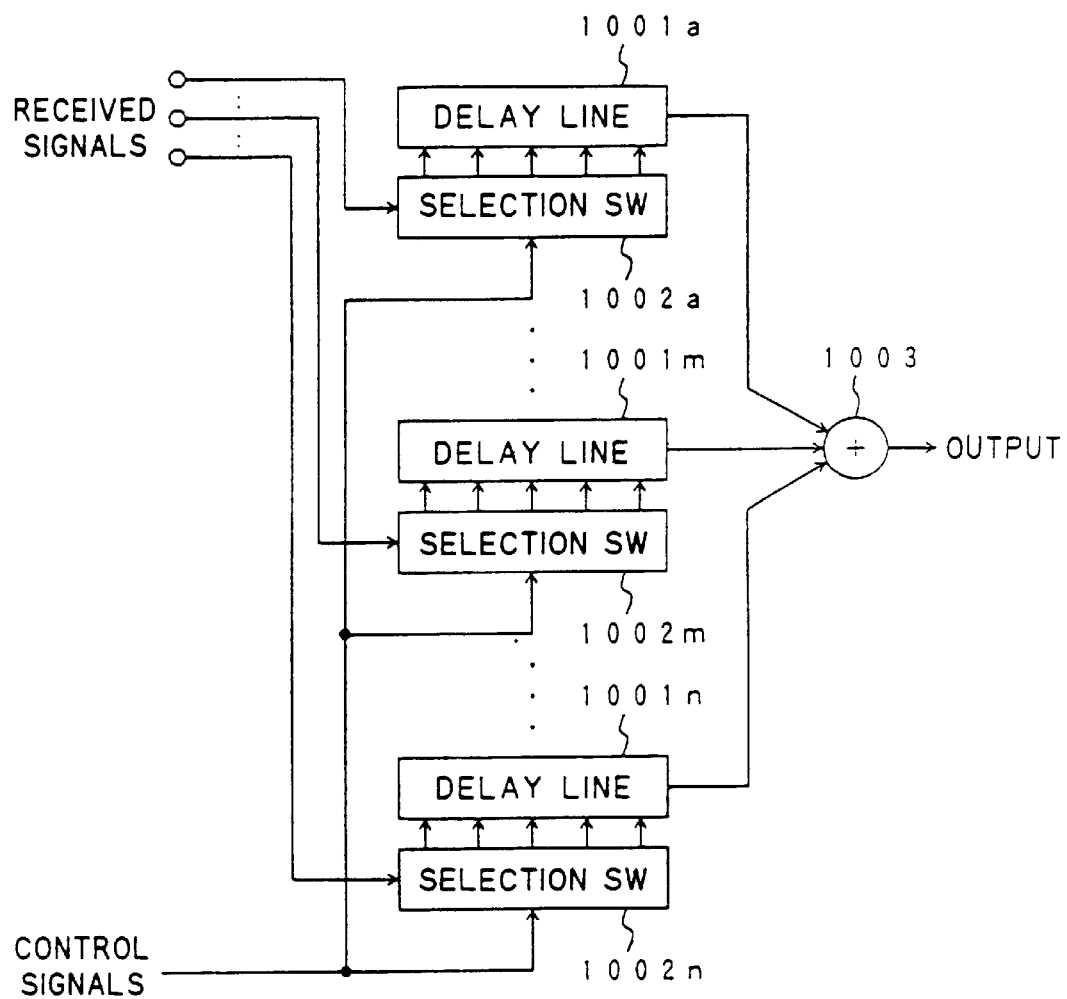

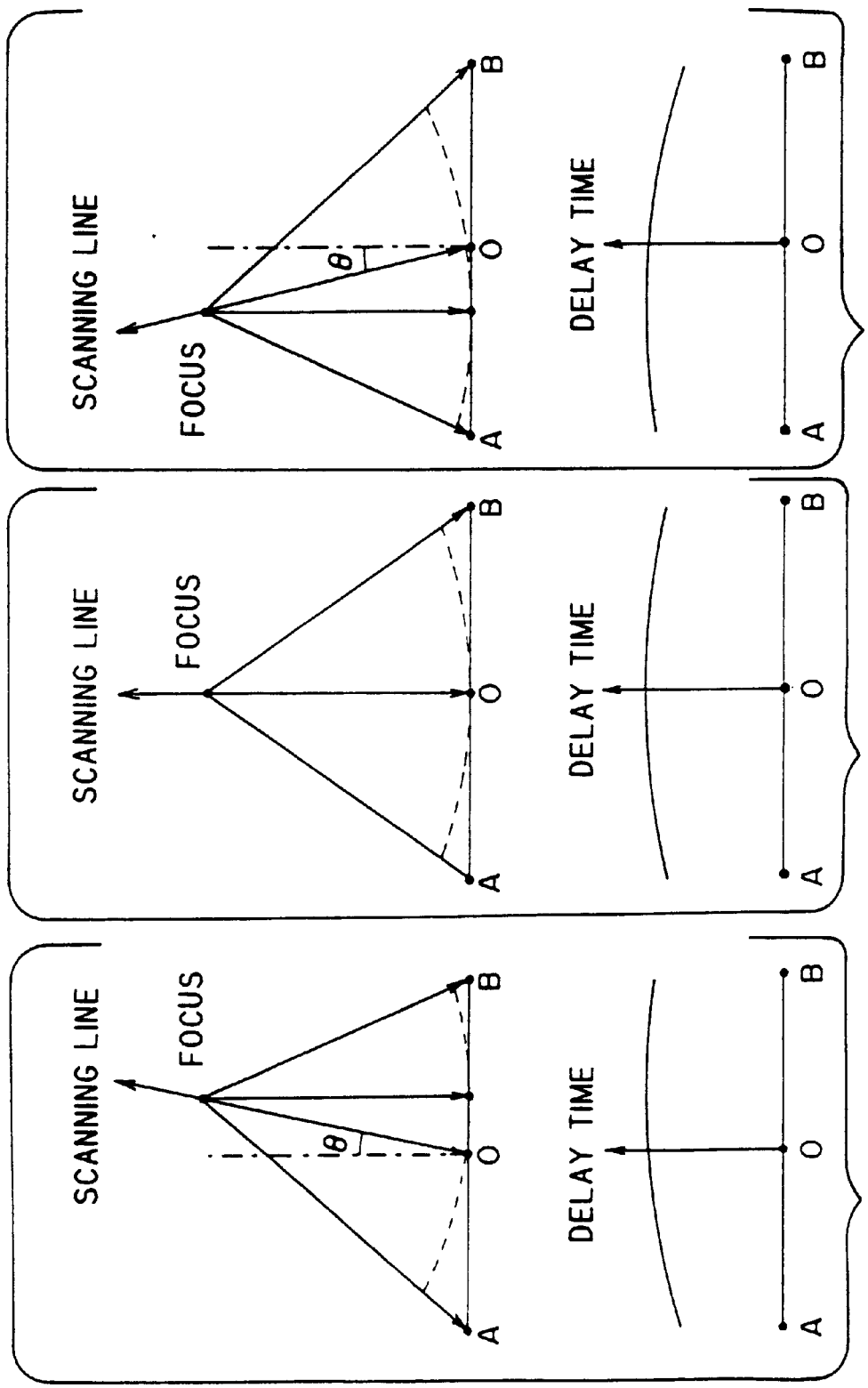

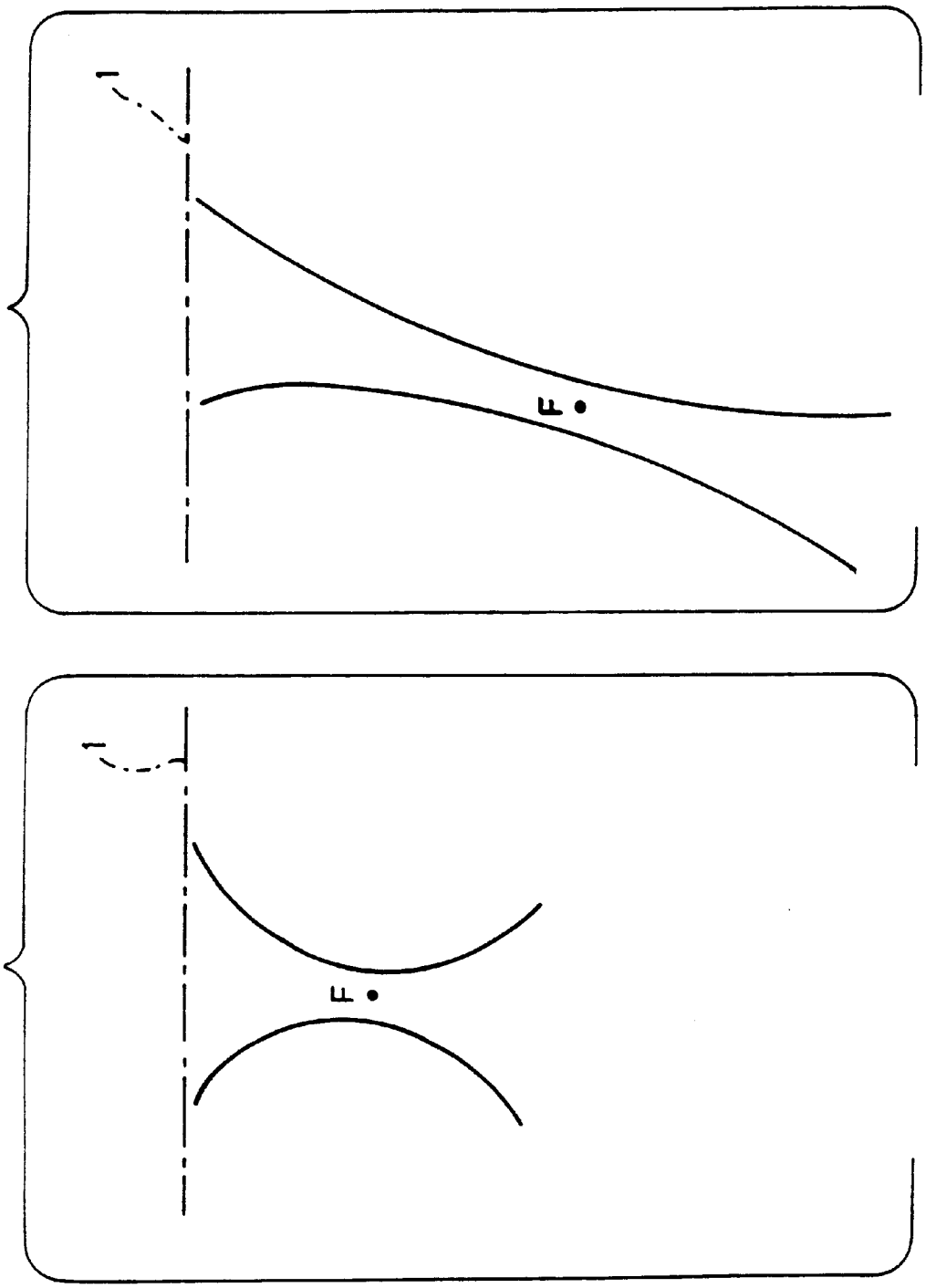

ULTRASONIC DIAGNOSTIC APPARATUS

This application is a divisional of application Ser. No. 08/974,517, filed Nov. 19, 1997, now allowed.

BACKGROUND OF THE INVENTION

1. Field of the Invention

The present invention relates to an ultrasonic diagnostic apparatus in which ultrasonic waves are transmitted into a subject, the ultrasonic waves reflected within the subject are received to obtain received signals, and an image is produced in accordance with the received signals. More particularly, the present invention relates to an ultrasonic diagnostic apparatus having a function of guiding a puncture needle to be introduced into a subject.

2. Description of the Related Art

Hitherto, there has been widely used for the purpose of diagnoses of a disease an ultrasonic diagnostic apparatus in which ultrasonic waves are transmitted into a subject, particularly, a human body, and the ultrasonic waves reflected at tissues within the subject are received to obtain received signals, so that an image is produced in accordance with the received signals thus obtained.

In some cases, it happens that for the purpose of picking of a part of tissues of the affected part for a diagnosis, while an image of the affected part within the subject, which is obtained with the use of the ultrasonic diagnostic apparatus as mentioned above, is observed, or for the purpose of injecting medical liquid into the affected part, a puncture needle is introduced into the affected part within the subject.

An ultrasonic diagnostic apparatus comprises, usually, an ultrasonic diagnostic apparatus main frame and an ultrasonic probe to be connected to the main frame. When a puncture needle is to be introduced into the subject, a guide member for guiding the puncture needle to be introduced into the subject is loaded onto the ultrasonic probe main body. The main body has a guide passage through which the puncture needle is introduced into the subject, so that the puncture needle is controlled by an operator in such a manner that it reaches a desired position while the operator observes an image of the seat of the disease.

The puncture needle is a hollow tube like an injection needle. For example, a tissue of the effected part is picked out through the tube of the puncture needle. The extracted tissue is submitted for a pathological examination and the like, and is used for a determination, for example, as to whether it is concerned with a malignant disease or a benign disease. Incidentally, while it was explained that the guide member is loaded onto the ultrasonic probe main body, it is acceptable that the ultrasonic probe main body and the guide member are formed into a unitary body. However, also in the following explanation, it will be continued assuming that the guide member is detachably loaded onto the ultrasonic probe main body.

FIG. 21 is a typical illustration of an ultrasonic probe in the state that a puncture needle is introduced into the subject. FIG. 22 is an illustration of an image by means of ultrasonic waves in such a state.

An ultrasonic probe 20 comprises a main frame 21 and a guide member 22 which is detachably loaded onto the main frame 21. On the tip of the main frame 21, there is arranged a plurality of ultrasonic transducers 211 (e.g. 128 pieces) as a circular arc by way of example. The ultrasonic transducers 211 are connected through a cable 212 to an ultrasonic diagnostic apparatus main frame (not illustrated).

To obtain an ultrasonic image, the tip of the ultrasonic probe 20 is put to the subject 1 so as to sequentially perform a transmit-receive operation for ultrasonic beams along a plurality of scanning lines 2 each extending from the tip of the ultrasonic probe into the subject 1. In this manner, a scan of the inside of the subject by a series of transmit-receive operations for ultrasonic beams makes it possible to obtain received signals representative of an ultrasonic image within a scanning area 3 defined by the plurality of scanning lines 2. The received signals thus obtained are subjected to various types of processing and then transmitted to an observation monitor television (not illustrated), so that the associated image within the scanning area 3 is displayed on a display screen 707a (cf. FIG. 22) of the observation monitor television.

To introduce a puncture needle 30 into the subject, the guide member 22 is loaded onto the main frame 21. As shown in FIG. 22, on an image screen, there is displayed a diagram 30a representative of a passage of the puncture needle 30, with being superposed on the image within the scanning area 3. The ultrasonic probe 20 is controlled in its position and direction to be put to the subject 1 so that an affected part 11 to which the puncture needle 30 is intended to be introduced and the diagram 30a indicative of the passage of the puncture needle 30 intersect. Under such a control of the ultrasonic probe 20, the puncture needle 30 is introduced into the subject 1 along a guide passage 22a of the guide member 22. In this manner, it is possible to introduce the puncture needle 30 into a desired position within the subject with a certain degree of reliability. Incidentally, in the above-description, while it was explained that the diagram 30a indicative of the passage of the puncture needle 30 is displayed on the display screen 707a, there is an ultrasonic diagnostic apparatus having no such a display function for the diagram.

When it is practiced such a puncture technique that a puncture needle is introduced into the subject to pick out tissues within the subject or inject a medical liquid into tissues within the subject, a low resolution of an image makes it difficult for an operator to exactly grasp a position of the puncture needle inserted into the subject. Further, it is difficult to adjust the tip of the puncture needle to a desired small point of the affected part 11. This is one of causes which make it difficult to exactly perform the puncture technique. Furthermore, even if there is displayed on the image screen a diagram indicative of the passage of the puncture needle, it happens that the puncture needle travels with being curved somewhat at the boundary of tissues within the subject, and thus the puncture needle does not always travel as indicated by the diagram. For these reasons, it is necessary to exactly grasp a position of the puncture needle indeed inserted into the subject. In the event that a position of the puncture needle cannot be exactly grasped, this is in danger of injuring blood vessels, internal organs or the like other than the site to which the puncture needle is intended to be introduced.

In order to solve these problem, there has been proposed a scheme in which a predetermined image area, which is located along a guidance direction for the puncture needle, is subjected to an image processing different from that for other image area, whereby it is easy to see the puncture needle on the image screen (cf. Japanese Patent Application Laid Open Gazette Sho. 63-290550).

The above-mentioned scheme fails to propose a solution as to what image processing is practiced to easily to see the puncture needle, although it is understood as to such a requirement that the puncture needle is displayed so as to be easy to see. Even if the puncture needle is displayed so as to be easy to see in accordance with the image processing, in order that the puncture needle reaches a desired point without injuring blood vessels, internal organs or the like other than the site to which the puncture needle is intended to be introduced, it is insufficient that only the puncture needle is displayed so as to be easy to see, and it is necessary to display also images of other than the puncture needle, for example, blood vessels, internal organs or the like within the subject.

Hitherto, there have been developed and proposed various types of image processings in which both the puncture needle and the blood vessels, internal organs or the like within the subject are subjected to an image processing in such a manner that they are easiest to see in the earlier technology of the field of the image processing. However, there remains such a problem that the position of the puncture needle is difficult to be grasped. Accordingly, the above-mentioned scheme such that the passage area of the puncture needle and another area are simply differentiated from each other in an image processing cannot implement an image which permits the position of the puncture needle to be exactly grasped, and also permits the puncture needle to reach a desired point without injuring blood vessels, internal organs or the like other than the site to which the puncture needle is intended to be introduced.

An image for an observation is usually determined in its resolution (e.g. density of scan lines 2 shown in FIG. 21) in view of the frame rate as an index indicative of the number of sheets of images capable of being obtained per unit time. To perform a puncture technique, there is a need to provide an image having a higher resolution than that of the image for an observation, and thus the image for an observation is essentially insufficient in its resolution. On the other hand, if it is intended that the resolution of the image is enhanced, then the frame rate will be decreased, since the resolution is determined in view of a balance with the frame rate, as mentioned above. As a result, a change of images cannot follow a velocity at which the puncture needle is introduced into the subject. This involves a problem which makes it difficult to perform a puncture technique with accuracy in the point of the frame rate.

Further, there is proposed such a technology that a tip portion of a puncture needle is vibrated by an oscillator to pick up a variation of the signals by a vibration, thereby exactly detect the tip position of the puncture needle (cf. U.S. Pat. No. 5,095,910). Specifically, according to the technology disclosed in U.S. Pat. No. 5,095,910, the tip position of the puncture needle is detected in such a manner that a Doppler transition of a frequency of ultrasonic waves reflected on the tip of the puncture needle, which occurs owing to the vibration of the tip of the puncture needle, is detected.

SUMMARY OF THE INVENTION

In view of the foregoing, it is therefore an object of the present invention to provide an ultrasonic diagnostic apparatus having a function of producing an image suitable for exactly practicing a puncture technique.

To achieve the above-mentioned objects, according to the present invention, there is provided a first ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer; and an image producing unit for producing an image based on the received signal, wherein said transmit-receive unit has a first transmit-receive mode in which said scanning area is scanned with a predetermined scanning density, and a second transmit-receive mode in which, of said scanning area, a predetermined first area including a part or a whole of a passage of the puncture needle is scanned with a scanning density higher than that of a second area, excepting the first area, of said scanning area.

According to the first ultrasonic diagnostic apparatus, there are provided the first transmit-receive mode in which said scanning area is scanned with a predetermined scanning density, that is, the transmit-receive mode for scanning the whole of the scanning area so as to obtain a resolution and a frame rate which are balanced with each other for an image observation, similar to that of the earlier technology, and in addition a second transmit-receive mode in which, of said scanning area, a predetermined first area including a part or a whole of a passage of the puncture needle is scanned with a scanning density higher than that of a second area, excepting the first area, of said scanning area, that is, the transmit-receive mode in which a resolution of the passage area (the first area) of the puncture needle is enhanced, even if a resolution of an area (the second area) other than the passage area (the first area) of the puncture needle is lowered. Thus, the use of the second transmit-receive mode makes it possible, when the puncture'technique is practiced, to improve the resolution of the passage of the puncture needle without greatly decreasing the frame rate, and makes it possible to grasp with sufficient accuracy the position of the puncture needle actually introduced and the arrangement position of tissues of the subject, and also to obtain an image capable of sufficiently following the rate of introducing of the puncture.

It is to be noted that the above-noted term "scanning density" implies the scanning density in the event that once transmit-receive of ultrasonic beams is countered as a piece of scanning line. Specifically, even if ultrasonic beams travelling along the same path are concerned, as known, a plurality of ultrasonic beams, which are mutually different in focal position, are sequentially transmitted and received thereby enhancing the resolution of images. Therefore, according to the present invention, in the event that even if ultrasonic beams travelling along the same path are concerned, the ultrasonic beams are transmitted and received a plurality of number of times on a sheet of image (frame), the number of pieces of scanning lines along the same path is countered as the same number of pieces as the number of times of transmit-receive of ultrasonic beams.

According to a second ultrasonic diagnostic apparatus, it is characterized by a second transmit-receive mode in which, of said scanning area, a predetermined first area including a part or a whole of a passage of the puncture needle is scanned with a scanning density higher than that of the first transmit-receive mode, instead of the second transmit-receive mode in which, of said scanning area, a predetermined first area including a part or a whole of a passage of the puncture needle is scanned with a scanning density higher than that of a second area, excepting the first area, of said scanning area, as in the first ultrasonic diagnostic apparatus.

According to the second ultrasonic diagnostic apparatus, in the second transmit-receive mode, the scanning on the second area referred to the first ultrasonic diagnostic apparatus according to the present invention is omitted. In a similar fashion to that of the first ultrasonic diagnostic apparatus according to the present invention, it is possible to provide images having a resolution and a frame rate easy to practice the puncture technique.

Here, in the first or second ultrasonic diagnostic apparatus, it is acceptable that the ultrasonic diagnostic apparatus further comprises a transmit-receive mode selection handler for optionally selecting between the first transmit-receive mode and the second transmit-receive mode. And it is also acceptable that said guide member is detachably loaded onto said main frame, said ultrasonic probe has a sensor for detecting whether said guide member is loaded onto said main frame, and said transmit-receive unit is switched in an operation mode between the first transmit-receive mode and the second transmit-receive mode according as a loading of said guide member onto said main frame is detected by said sensor or not. In this case, it is preferable that said sensor detects whether said guide member is loaded onto said main frame, and in addition identifies a type of the guide member loaded onto the main frame, and said transmit-receive unit sets up the first area in accordance with the type of the guide member.

Since a direction of introducing a puncture needle into the subject is determined in accordance with the guide member, for permitting a puncture needle to be introduced into the different depth position of the subject, it is necessary to provide a plurality of guide members detachably loaded onto the main frame, mutually different in direction of introducing a puncture needle into the subject. In this case, it is considered that there will occur a necessity of varying the first area to improve the resolution in accordance with types of the guide members. For this reason, the sensor is provided with the function of identifying a type of the guide member loaded, and the first area is set up in accordance with the type of the guide member loaded. This feature makes it possible to significantly improve an operability as compared with an arrangement in which the first area is controlled to meet the guide member loaded through an operation by a handler, for example.

In the first or second ultrasonic diagnostic apparatus, it is acceptable that the ultrasonic diagnostic apparatus further comprises an oscillation mechanism for vibrating a tip of the puncture needle, and said transmit-receive unit receives vibrations of the tip of the puncture needle transferred to the ultrasonic transducer, detects a position of the tip of the puncture needle, and sets up the first area in accordance with a detected position of the tip of the puncture needle.

Further, it is acceptable that said ultrasonic probe has a sensor for measuring a length of a portion of a tip end of the puncture needle passing through said guide member, and said transmit-receive unit sets up the first area in accordance with the length measured by said sensor.

In the first or second ultrasonic diagnostic apparatus, it is acceptable that said image producing unit has a function of superimposing a figure representative of the passage of the puncture needle on an image based on the received signal; said ultrasonic diagnostic apparatus has a figure superimposing selection handler for performing a selection as to whether the figure is to be superimposed on the image; and said transmit-receive unit is switched in an operation mode between the first transmit-receive mode and the second transmit-receive mode according as said figure superimposing selection handler selects a state that the figure is to be superimposed on the image, or not.

As mentioned above, in the event that there is provided the handler for performing an operation associated with the puncture technique, a plurality of operations associated with the puncture technique may be simultaneously selected through a single handler thereby improving an operability.

Further, in the first or second ultrasonic diagnostic apparatus, it is preferable that said image producing unit has a first image producing mode for producing a first image representative of the whole area of said scanning area, and a second image producing mode for producing a second image representative of an enlarged area consisting of a partial area including at least part of the passage of the puncture needle, of said scanning area, or an enlarged area consisting of the whole area of said scanning area, a size per unit area within the subject of the second image being enlarged more than the first image.

This feature makes it possible to not only improve a resolution, but also to provide an enlarged image which is more preferable and easy to see for the puncture technique.

In the aspect, it is acceptable that the ultrasonic diagnostic apparatus further comprises an image producing mode selection handler for optionally selecting between the first image producing mode and the second image producing mode. It is also acceptable that said guide member is detachably loaded onto said main frame, said ultrasonic probe has a sensor for detecting whether said guide member is loaded onto said main frame, and said image producing unit is switched in an operation mode between the first image producing mode and the second image producing mode according as a loading of said guide member onto said main frame is detected by said sensor or not. In a case where the sensor is provided, it is preferable that said sensor detects whether said guide member is loaded onto said main frame, and in addition identifies a type of the guide member loaded onto the main frame, and said image producing unit sets up the enlarged area in accordance with the type of the guide member.

As mentioned above, a guiding direction of a puncture needle into the subject is varied in accordance with types of the guide member. In this case, it happens that it is preferable that the enlarged area is varied in accordance with types of the guide members. For this reason, the sensor is provided with the function of identifying a type of the guide member loaded, and the enlarged area is set up in accordance with the type of the guide member loaded. This feature makes it possible to significantly improve an operability as compared with an arrangement in which the enlarged area is manually set up.

In the aspect having the first image producing mode and the second image producing mode in the first or second ultrasonic diagnostic apparatus, it is acceptable that the ultrasonic diagnostic apparatus further comprises an oscillation mechanism for vibrating a tip of the puncture needle, wherein said transmit-receive unit receives vibrations of the tip of the puncture needle transferred to the ultrasonic transducer, and detects a position of the tip of the puncture needle, and said image producing unit sets up the enlarged area in accordance with a detected position of the tip of the puncture needle.

It is also acceptable that said ultrasonic probe has a sensor for measuring a length of a portion of a tip end of the puncture needle passing through said guide member, and said image producing unit sets up the enlarged area in accordance with the length measured by said sensor.

Further, in the aspect having the first image producing mode and the second image producing mode in the first or second ultrasonic diagnostic apparatus, it is acceptable that said image producing unit has a function of superimposing a figure representative of the passage of the puncture needle on an image based on the received signal; said ultrasonic diagnostic apparatus has a figure superimposing selection handler for performing a selection as to whether the figure is to be superimposed on the image; and said image producing unit is switched in an operation mode between the first image producing mode and the second image producing mode according as said figure superimposing selection handler selects a state that the figure is to be superimposed on the image, or not.

In a similar fashion to that of a selection between the first transmit-receive mode and the second transmit-receive mode, as mentioned above, the common use of the figure superimposing selection handler for selection between the first image producing mode and the second image producing mode makes it possible to enhance the operability.

To achieve the above-mentioned objects, according to the present invention, there is provided a third ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer;

an image producing unit for producing an image based on the received signal; and an oscillation mechanism for vibrating a tip of the puncture needle, wherein said transmit-receive unit receives vibrations of the tip of the puncture needle transferred to the ultrasonic transducer, detects a position of the tip of the puncture needle, and drives said ultrasonic transducer so as to form the ultrasonic beam having a frequency according to a detected position of the tip of the puncture needle.

While transmit-receive of the ultrasonic beam having a high frequency makes it possible to improve a resolution, the ultrasonic beam having a high frequency involves a great amount of attenuation. Thus, it is difficult to obtain images on deep portions within the subject. In view of the foregoing, when the tip of the puncture needle is located at the shallow site within the subject in accordance with the position of the tip of the puncture needle detected, a high frequency of ultrasonic beam is used for the transmit-receive to improve the resolution of images. On the other hand, as the tip of the puncture needle is introduced into the deep portion of the subject, a lower frequency of ultrasonic beam is used for the transmit-receive. Thus, it is possible to produce a high resolution of image in its entirety as much as possible.

To achieve the above-mentioned objects, according to the present invention, there is provided a fourth ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer;

an image producing unit for producing an image based on the received signal; and an oscillation mechanism for vibrating a tip of the puncture needle, wherein said transmit-receive unit receives vibrations of the tip of the puncture needle transferred to the ultrasonic transducer, detects a position of the tip of the puncture needle, and drives said ultrasonic transducer so as to form the ultrasonic beam with a period according to a detected position of the tip of the puncture needle.

While shortening a period of the formation of the ultrasonic beam makes it possible to improve a frame rate, and if the frame rate is maintained constant, then it is possible to improve a resolution through increasing the number of scanning lines, there is a limit in shortening of the period, since time is required for propagation of the ultrasonic beam as to transmitting the ultrasonic beam up to a deep position within the subject and receiving the ultrasonic beam reflected on the deep position. In view of the foregoing, when the tip of the puncture needle is located at the shallow site within the subject, a period of transmit-receive of ultrasonic beam is shortened to improve the frame rate or the resolution of images. On the other hand, as the tip of the puncture needle is introduced into the deep portion of the subject, a period of transmit-receive of ultrasonic beam is extended. Thus, it is possible to obtain images controlled with a high level in the frame rate and the resolution in its entirety.

To achieve the above-mentioned objects, according to the present invention, there is provided a fifth ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer;

an image producing unit for producing an image based on the received signal; and an oscillation mechanism for vibrating a tip of the puncture needle, wherein said transmit-receive unit receives vibrations of the tip of the puncture needle transferred to the ultrasonic transducer, detects a position of the tip of the puncture needle, and drives said ultrasonic transducer so as to vary a focal distance of the ultrasonic beam in accordance with a detected position of the tip of the puncture needle.

When the puncture technique is practiced, an area or region of the most interest is the area of the vicinity of the tip of the puncture needle. Consequently, it is preferable that a resolution of the image of such an area is improved. On the other hand, a beam diameter of an ultrasonic beam is not even along the longitudinal direction of the ultrasonic beam. The ultrasonic beam is provided with a focus having the finest beam diameter at a certain depth position. A resolution is enhanced with the finer beam diameter. Thus, a focus of the ultrasonic beam is formed at the depth position according to the position of the tip of the puncture needle, thereby producing a high resolution of image suitable for the puncture technique.

To achieve the above-mentioned objects, according to the present invention, there is provided a sixth ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer; and an image producing unit for producing an image based on the received signal, wherein said ultrasonic probe has a sensor for measuring a length of a portion of a tip end of the puncture needle passing through said guide member, and said transmit-receive unit drives said ultrasonic transducer so as to form the ultrasonic beam having a frequency according to a length measured by said sensor.

According to the sixth ultrasonic diagnostic apparatus, a frequency of the ultrasonic wave is altered in accordance with a length of a portion of a tip of the puncture needle introduced. This feature makes it possible to produce a higher resolution of image in accordance with a length of a portion of a tip of the puncture needle introduced as much as possible, similar to the third ultrasonic diagnostic apparatus.

To achieve the above-mentioned objects, according to the present invention, there is provided a seventh ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer; and an image producing unit for producing an image based on the received signal, wherein said ultrasonic probe has a sensor for measuring a length of a portion of a tip end of the puncture needle passing through said guide member, and said transmit-receive unit drives said ultrasonic transducer so as to sequentially form ultrasonic beams with a period according to a length measured by said sensor.

According to the seventh ultrasonic diagnostic apparatus, similar to the fourth ultrasonic diagnostic apparatus, a period for formation of the ultrasonic beam is controlled. This feature makes it possible to produce images suitable for the puncture technique, controlled with high level in the frame rate and the resolution.

To achieve the above-mentioned objects, according to the present invention, there is provided an eighth ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said ultrasonic transducer to sequentially generate ultrasonic waves travelling along the plurality of scanning lines, and deriving received signals by means of receiving by the ultrasonic transducer ultrasonic waves reflected within the subject and returned to the ultrasonic transducer; and an image producing unit for producing an image based on the received signal, wherein said ultrasonic probe has a sensor for measuring a length of a portion of a tip end of the puncture needle passing through said guide member, and said transmit-receive unit drives said ultrasonic transducer so as to vary a focal distance of the ultrasonic beam in accordance with a length measured by said sensor.

According to the eighth ultrasonic diagnostic apparatus, a focal position of the ultrasonic beam is controlled in accordance with a length of a portion of a tip of the puncture needle introduced. This feature makes it possible to produce a higher resolution of image suitable for the puncture technique, similar to the fifth ultrasonic diagnostic apparatus.

Here, while it is acceptable that the first to eighth ultrasonic diagnostic apparatus are to produce images on the plane scanning area spreading on a two-dimensional basis, it is preferable that transmission and reception of ultrasonic beams along a plurality of scanning lines arranged on a three-dimensional basis extending to the inside of the subject are repeatedly performed to scan the inside of the subject, and an image on a three-dimensional scanning area defined by the plurality of scanning lines is produced in accordance with a received signal obtained by the scanning.

As mentioned above, when the puncture needle is introduced into the subject, it happens that the puncture needle does not always travel along a predetermined passage, but makes a turn owing to a difference between tissues in toughness at the boundary of tissues within the subject, and travels along a path out of the predetermined passage. In addition, it happens that the puncture needle makes a turn in a direction out of the two-dimensional surface plane. In such a case, simply displaying the two-dimensional tomographic image may invite such a result that the tip of the puncture needle is out of the displayed image and thus an operator cannot sufficiently observe the tip of the puncture needle. For these reasons, the three-dimensional scanning area is formed to obtain the three-dimensional image. This feature makes it possible to always exactly monitor the tip of the puncture needle.

Incidentally, it is to be noted that since a lot of time is required for a constitution of the three-dimensional image, it is preferable that the constitution of the three-dimensional image is effected on only the area or region of the vicinity of the passage of the puncture needle.

BRIEF DESCRIPTION OF THE DRAWINGS

FIG. 3 is a conceptual view showing delay patterns of high voltage pulses to be applied to a plurality of ultrasonic transducers;

FIGS. 4(A) and 4(B) are typical illustrations each a state in which a high voltage pulse train having different pulse width and repetitive period is applied to an ultrasonic transducer;

FIG. 5 is a diagram used for the explanation of the principle of a formation of a received ultrasonic beam in the beamformer;

FIGS. 6(A), 6(B) and 6(C) are explanatory views each showing a relationship among a delay pattern, a direction of a scanning line and a point of a focus;

FIGS. 17(A) and 17(B) are illustrations each showing a beam configuration of ultrasonic beams;

DESCRIPTION OF THE PREFERRED EMBODIMENTS

Hereinafter, there will be described embodiments of the present invention.

Figure 1:
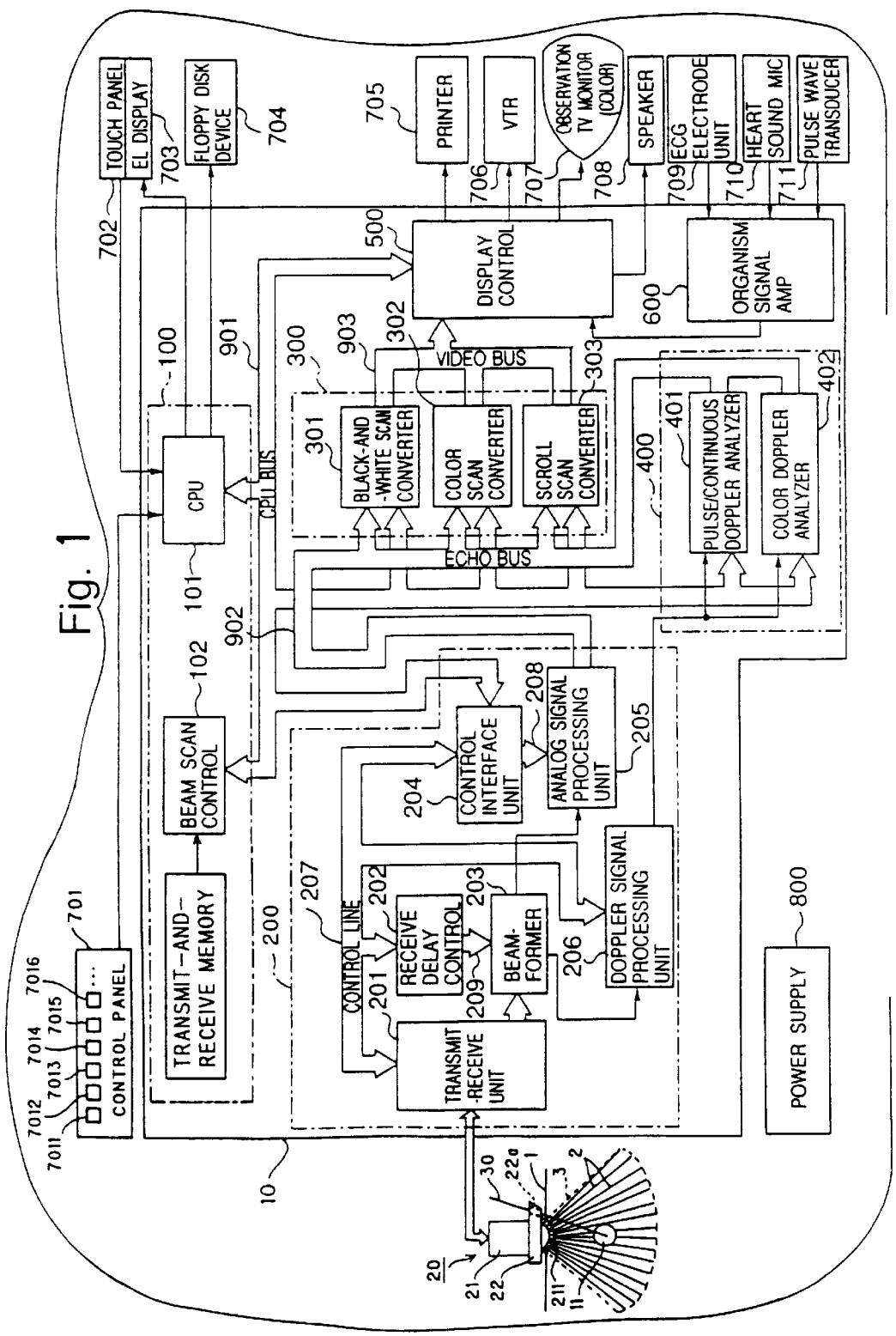
FIG. 1 is a block diagram of an ultrasonic diagnostic apparatus according to an embodiment of the present invention.

FIG. 1 is a block diagram of an ultrasonic diagnostic apparatus according to an embodiment of the present invention. There will be described an outline of the ultrasonic diagnostic apparatus referring to this block diagram. First, there will be described a structure of the ultrasonic diagnostic apparatus hereinafter.

A main frame 10 of the ultrasonic diagnostic apparatus comprises a control unit 100, an analog processing unit 200, a digital scan converter unit 300, a Doppler processing unit 400, a display control unit 500 and an organism signal amplifier unit 600. The control unit 100 comprises a CPU 101, a beam scan control unit 102 and a transmit-and-receive memory 103. Connected to the CPU 101 are a control panel 701, a unitary body of touch panel 702 and EL display 703, and a floppy disk device 704.

The analog processing unit 200 comprises a transmit-receive unit 201, a receive delay control unit 202, a beamformer unit 203, a control interface unit 204, an analog signal processing unit 205 and a Doppler signal processing unit 206. The control interface unit 204, the transmit-receive unit 201, the receive delay control unit 202, and the Doppler signal processing unit 206 are connected to one another via a control line 207. Further, the control interface unit 204 is connected via a control line 208 to the analog signal processing unit 205. The receive delay control unit 202 and the beamformer unit 203 are connected to one another via a control line 209. Detachably connected to the transmit-receive unit 201, which constitutes the analog processing unit 200, is an ultrasonic probe 20, by the maximum, four pieces of ultrasonic probe 20.

The digital scan converter unit 300 comprises a black-and-white scan converter 301, a color scan converter 302 and a scroll scan converter 303.

The Doppler processing unit 400 comprises a pulse/continuous wave Doppler analyzing unit 401 and a color Doppler analyzing unit 402.

The display control unit 500 is illustrated with a single block. Connected to the display control unit 500 are a printer 705, a VTR (Video Tape Recorder) 706, an observation television monitor 707 and a speaker 708.

The organism signal amplifier unit 600 is also illustrated with a single block. Connected to the organism signal amplifier unit 600 are an ECG electrode unit 709, a heart sound microphone 710 and a pulse wave transducer 711.

The ultrasonic diagnostic apparatus further comprises a power source unit 800 connected to a commercial power supply for supplying necessary power to individual sections of the ultrasonic diagnostic apparatus.

The main frame 10 has a CPU bus 901 for connecting the CPU 101 and the beam scan control unit 102, which constitute the control unit 100, the control interface unit 204, which constitutes the analog processing unit 200, the black-and-white scan converter 301, the color scan converter 302 and the scroll scan converter 303, which constitute the digital scan converter unit 300, the pulse/continuous wave Doppler analyzing unit 401 and the color Doppler analyzing unit 402, which constitute the Doppler processing unit 400, and the display control unit 500 with each other. The main frame 10 further has an echo bus 902 for supplying image data generated from the analog signal processing unit 205, which constitutes the analog processing unit 200, to the digital scan converter unit 300. With respect to data generated from the pulse/continuous wave Doppler analyzing unit 401 and the color Doppler analyzing unit 402, which constitute the Doppler processing unit 400, such data are also supplied through the echo bus 902 to the digital scan converter unit 300. The main frame 10 further has a video bus 903 for transmitting a video signal generated from anyone of the black-and-white scan converter 301, the color scan converter 302 and the scroll scan converter 303, which constitute the digital scan converter unit 300, to the display control unit 500.

The control panel 701 consists of a keyboard, etc. having a number of keys arranged, including a number of handlers 7011, 7012, 7013, 7014, 7015, 7016. When the control panel 701 is operated, operation information is detected by the CPU 101, so that an instruction associated with the operation information is transmitted to the beam scan control unit 102, the control interface unit 204, the digital scan converter unit 300, or the display control unit 500 in accordance with the the instruction.

The EL display unit 703 has a liquid-crystal display screen. The CPU 101 serves as an EL line drawing generating unit for generating an EL line drawing to be displayed on the liquid-crystal display screen of the EL display unit 703, too. The EL line drawing generated in the CPU 101 is displayed on the liquid-crystal display screen of the EL display unit 703. The liquid-crystal display screen of the EL display unit 703 is provided with the touch panel 702. When an operator touches the touch panel 702 by his fingers, position information representative of the associated touched position on the touch panel 702 is transmitted to the CPU 101. The touch panel 702 and the EL display unit 703 are arranged, so that various types of instructions to the ultrasonic diagnostic apparatus can be readily inputted, in such a manner that, for instance, when it is instructed to the ultrasonic diagnostic apparatus through an operation of the control panel 701 that a parameter as to a certain mode is set up for the ultrasonic diagnostic apparatus, the CPU 101 causes the EL display unit 703 to display a table of a number of parameters to be set up for the selected mode, so that an operator touches the touch panel 702 by his fingers to set up a desired parameter.

The floppy disk device 704 is a device onto which a floppy disk (not illustrated) is detachably loaded, wherein the loaded floppy disk is accessed. The CPU 101 causes instructions made by an operator through an operation of the control panel 701 and the touch panel 702 to be written into the floppy disk loaded onto the floppy disk device 704. When the power supply of the ultrasonic diagnostic apparatus is turned on, or when a reset to the initial state is instructed through an operation of the control panel 701, various types of instruction information, which are stored in the floppy disk device 704 loaded onto the floppy disk device 704, are read out therefrom and fed to the CPU 101 so that the CPU 101 sets up the individual sections of the ultrasonic diagnostic apparatus to the initial state in accordance with the instruction information. There will exist a number of parameters to be set up by an operator through an operation of the control panel 701 and the touch panel 702, which are needed when the ultrasonic diagnostic apparatus is operated. It will be very troublesome for the operator to do over again a setting of such a number of parameters, for example, whenever the power supply turns on. For this reason, parameters of the initial state, etc. are written in the floppy disk beforehand, and when the power supply of the ultrasonic diagnostic apparatus is turned on, or when a reset to the initial state is instructed, the parameters and the like stored in the floppy disk are read out therefrom to set up the individual sections of the ultrasonic diagnostic apparatus in accordance with the parameters and the like thus read, thereby contributing to an enhancement of efficiency in setting the parameters and the like.

The CPU 101, which constitutes the control unit 100, mainly serves as a man-machine interface, as mentioned above. On the other hand, the beam scan control unit 102, which also constitutes the control unit 100, is mainly in charge of the control, for example, of timing of transmit and receive of ultrasonic waves in the ultrasonic diagnostic apparatus, which needs an operational ability on a real-time basis. According to this type of ultrasonic diagnostic apparatus, when transmit and receive of ultrasonic waves are performed, data for controlling the individual sections constituting the analog processing unit 200 are read from a transmit-and-receive memory 103, and the data thus read from the transmit-and-receive memory 103 are transmitted from the beam scan control unit 102 through the CPU bus 901 to the control interface unit 204, so that the control interface unit 204 controls via a control line 207 the transmit-receive unit 201, the receive delay control unit 202, and the Doppler signal processing unit 206. Further, the control interface unit 204 controls via a control line 208 the analog signal processing unit 205. The receive delay control unit 202 controls the beamformer unit 203 via the control line 209 under control of the control interface unit 204. With respect to the control of the individual sections of the analog processing unit 200 by the data read from the transmit-and-receive memory 103, it will be described in detail later.

The transmit-receive unit 201 is coupled to the ultrasonic probe 20. With respect to the ultrasonic probe, there exist, for example, a linear scan type of ultrasonic probe, a convex scan type of ultrasonic probe, and a sector scan type of ultrasonic probe. As an especial type of ultrasonic probe, there is a type of ultrasonic probe to be inserted into a body cavity. Further, with respect to those various types of ultrasonic probes, there exist many types of ultrasonic probes, which may be classified in accordance with a difference in frequency of the ultrasonic waves to be used. In order that a ultrasonic probe is loaded on the main frame 10, a connector (not illustrated) is used. The main frame 10 end is provided with four connectors adapted to be connected to ultrasonic probes. Thus, as mentioned above, it is possible to simultaneously load onto the connectors the ultrasonic probes, by the maximum 4 pieces, of the above-mentioned various types of ultrasonic probes. When a ultrasonic probe is loaded on the main frame 10, the main frame 10 may identify information as to which type of ultrasonic probe is loaded. Such information is transmitted via the control line 207, the control interface unit 204 and the CPU bus 901 to the CPU 101. On the other hand, the control panel 701 issues through an operation of the handler 7011 an instruction as to which ultrasonic probe is used among the ultrasonic probes connected to four connectors of the main frame 10 end, when the ultrasonic diagnostic apparatus is used. Such an instruction is transmitted via the CPU bus 901 to the beam scan control unit 102. Upon receipt of such an instruction, the beam scan control unit 102 reads out from the transmit-and-receive memory 103 data associated with the ultrasonic probe to be used. The data thus read is transmitted via the CPU bus 901, the control interface unit 204 and the control line 207 to the transmit-receive unit 201. Upon receipt of the instruction, the transmit-receive unit 201 transmits high voltage pulses (which will be described latter) to the ultrasonic probe 20 thus indicated to generate ultrasonic waves, and receives signals which are received by the ultrasonic probe 20. Here, it is assumed that the ultrasonic probe 20, as shown in FIG. 1 by one, is selected for transmission and reception of ultrasonic waves.

The ultrasonic probe 20 shown in FIG. 1 is a so-called convex scanning type of ultrasonic probe. On the tip of the ultrasonic probe 20, there are arranged a plurality of ultrasonic transducers 211, which are put to a surface of the subject 1 (particularly human body) to transmit and receive ultrasonic waves. In this condition, high voltage pulses for transmission and reception of ultrasonic waves are applied from the transmit-receive unit 201 to the plurality of ultrasonic transducers 211, respectively. The high voltage pulses applied to the plurality of ultrasonic transducers 211 are controlled in a relative time difference under control of the control interface unit 204. Ultrasonic pulse beams are transmitted from the plurality of ultrasonic transducers 211 along anyone of a plurality of scan lines 2 extending to the inside of the subject 1 in such a manner that the focus of the ultrasonic pulse beams is adjusted on a predetermined depth position inside of the subject 1 in accordance with a control of the relative time difference as to the application of the high voltage pulses to the plurality of ultrasonic transducers 211.

With respect to the attribute of the ultrasonic pulse beams to be transmitted, that is, a direction, a depth position of the focus, and a center frequency, etc. of the ultrasonic pulse beams, their associated data are essentially stored in the transmit-and-receive memory 103. And thus the ultrasonic transducers 211 transmits ultrasonic pulse beams which are determined by data read out from the transmit-and-receive memory 103 and transferred via the CPU bus 901 to the control interface unit 204 under control of the beam scan control unit 102.

The ultrasonic pulse beam is reflected on the individual points on the one scan line during travelling inside the subject 1, and returns to the ultrasonic probe 20 so that the reflected ultrasonic waves are received by the plurality of ultrasonic transducers 21. A plurality of signals, which are obtained through receiving the reflected ultrasonic waves, are supplied to the transmit-receive unit 201 so as to be amplified by a plurality of preamplifiers (not illustrated) of the transmit-receive unit 201, and then fed to the beamformer unit 203. The beamformer unit 203 is provided with an analog delay line (which will be described later) having a number of center taps. The center taps are selected in operation to receive the plurality of signals transmitted from the transmit-receive unit 201 in accordance with a control of the receive delay control unit 202, whereby the plurality of signals are relatively delayed and added together in current. Controlling a relative delay pattern as to the plurality of signals may emphasize the reflected ultrasonic waves in the direction along the scan line identical with the scan line associated with the time of the ultrasonic wave transmission, and forms a so-called received beam in which the focus of the ultrasonic pulse beams is adjusted on a predetermined depth position inside of the subject 1. Since ultrasonic waves travel slowly inside of the subject 1 as compared with a rate of the signal processing, it is possible to implement a so-called dynamic focus in which the focus is sequentially shifted to the deeper position inside of the subject while receiving the ultrasonic waves along one scan line. In this case, the center taps of the analog delay line are switchingly selected by the receive delay control unit 202 in response to the signals sequentially obtained by the ultrasonic transducers, even during once receiving associated with once transmitting the ultrasonic pulse beam.

Also with respect to the attribute of the received ultrasonic beams, that is, a direction, and a depth position of the focus, etc. of the received ultrasonic beams, they are determined in accordance with their associated data essentially stored in the transmit-and-receive memory 103. That is, data, which are stored in the transmit-and-receive memory 103, are read out from the transmit-and-receive memory 103 and transferred via the CPU bus 901 to the control interface unit 204 under control of the beam scan control unit 102, and further transferred via the control line 207 to the receive delay control unit 202. The receive delay control unit 202 controls the beamformer unit 203 in accordance with the data thus transmitted thereto.

According to the above-mentioned explanation, the high voltage pulses are applied to the ultrasonic transducers 211 to transmit the ultrasonic pulse beam. In this case, as mentioned above, since ultrasonic waves travel slowly inside of the subject as compared with a rate of the signal processing, it is possible, through measuring time from a starting time of application of the high voltage pulses to the ultrasonic transducers 211 to a time of receive of the reflected ultrasonic waves by the ultrasonic transducers 211, to identify the signal obtained at that time concerned with receiving of the reflected ultrasonic waves with respect to the association of the reflected ultrasonic wave with the depth position inside of the subject. That is, the feature that the ultrasonic wave to be transmitted is shaped as a pulse may provide a resolution with respect to the depth direction of the subject. Usually, in this manner, the high voltage pulses are applied to the ultrasonic transducers 211. In the special case, however, on condition that it is permitted to have no resolution with respect to the depth direction of the subject, it happens that a continuously repetitive high voltage pulse train signal is applied to the ultrasonic transducers 211 to transmit ultrasonic beams in the form of a continuous wave.

Also hereinafter, the ultrasonic diagnostic apparatus will be explained on the assumption that a pulse-like shaped ultrasonic beam is transmitted, except for a case that when the pulse/continuous wave Doppler analyzing unit 401, which constitutes the Doppler processing unit 400, is explained, the continuous wave is referred to.

Figure 21:
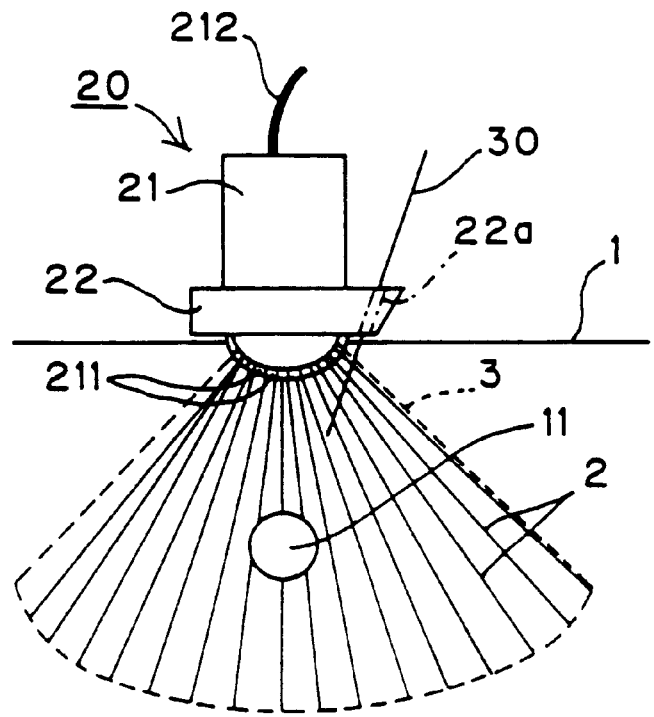
FIG. 21 is a typical illustration of an ultrasonic probe in the state that a puncture needle is introduced into the subject.
Figure 22:
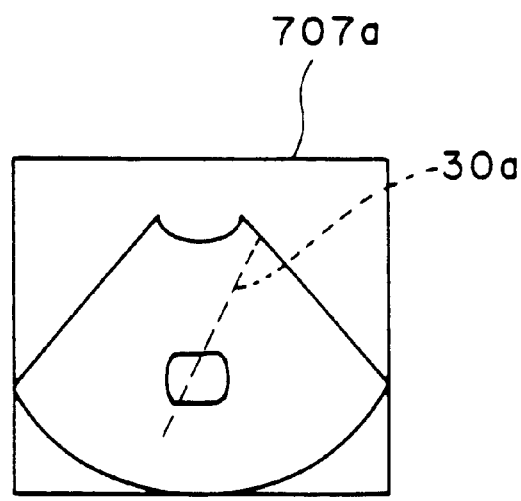
FIG. 22 is an illustration of an example of an image by means of ultrasonic waves in the state that a puncture needle is introduced into the subject.

The ultrasonic probe 20 shown in FIG. 1 comprises, in a similar fashion to that of the ultrasonic probe according to the earlier development explained referring to FIG. 21, a main frame 21 having a plurality of ultrasonic transducers 211 arranged, and a guide member 22 which is detachably loaded onto the main frame 21. The guide member 22 has a guide passage 22a for guiding the puncture needle 30 so that the puncture needle 30 can be introduced into the subject 1 within a scanning area 3 defined by a plurality of scanning lines 2 and in a predetermined direction. Thus, the puncture needle 30 is inserted into the guide passage 22a to be introduced to the affected part 11 within the subject 1.

In the manner as mentioned above, the transmit-receive unit 201 and the beamformer unit 203 sequentially repeatedly perform transmission and reception of the ultrasonic pulse beams along each of a plurality of scanning lines 2 inside of the subject 1, so that scanning line signals thus generated, each representative of the received ultrasonic beam along each of the scanning lines, are sequentially fed to the analog signal processing unit 205. In the analog signal processing unit 205, the received scanning line signals are subjected to logarithmic compression, detection, and filtering processings, etc. according to a designation issued through an operation of the handler 7012 of the control panel 701 as to which depth area inside of the subject 1 an image is to be displayed concerned with, that is, a designation as to whether it is sufficient that an image concerned with only the shallow area inside of the subject 1 is displayed, or a designation as to what degree of depth area an image is to be displayed concerned with. The analog signals thus processed are converted into digital of image data by an A/D converter unit. Image data outputted from the analog signal processing unit 205 are fed via the echo bus 902 to the black-and-white scan converter 301, which constitutes the digital scan converter unit 300. The black-and-white scan converter 301 performs an interpolation processing for generating data associated with pixels for a display, and converts the received image data to a video signal for a display, and then transmits the video signal for a display via the video bus 903 to the display control unit 500. The display control unit 500 causes the observation television monitor 707 to display a B-mode image caused by the ultrasonic reflection intensity distribution on the tomographic plane of the subject defined by a plurality of scanning lines 2. At that time, if necessary, it is possible to display patient's names, photographing date, photographing conditions, etc. superposing on the B-mode image. As the B-mode image, it is possible to display a dynamic image representative of the state in which the inside of the subject 1 moves, a static image at a certain time, or an image in a certain phase of a movement of the heart of a human body, which is synchronized with the movement of the heart, in accordance with a synchronizing signal generated from the organism signal amplifier unit 600.

Connected to the organism signal amplifier unit 600 are the ECG electrode unit 709, the heart sound microphone 710 and the pulse wave transducer 711. The organism signal amplifier unit 600 generates the synchronizing signal in accordance with any one of these elements or a plurality of sensors, and transmits the same to the display control unit 500.

Connected to the display control unit 500 are the observation television monitor 707, and the printer 705 and the VTR 706 as well. The display control unit 500 outputs images displayed on the observation television monitor 707 to the printer 705 or the VTR 706 in accordance with an instruction from an operator.

Again, an explanation will be continued from the analog processing unit 200.

When it is desired to know time variation of information as to the reflection of ultrasonic waves on a certain one scan line extending to the inside of the subject, the ultrasonic waves are repeatedly transmitted and received along a certain one scanning line of interest, and data representative of the received ultrasonic beam of the subject along the one scan line is transmitted via the echo bus 902 to the scroll scan converter 303. The scroll scan converter 303 generates a video signal representative of an image (an M-mode image) in which the ultrasonic reflection intensity distribution in the depth direction of the subject along the one scan line is given in the longitudinal direction, and the lateral axis consists of a time axis, wherein the image is scrolled in the time axis direction. The video signal thus generated is fed via the video bus 903 to the display control unit 500, so that an image based on the video signal is displayed, for example, on the observation television monitor 707.

The display control unit 500 has a function such that the video signal representative of the B-mode image transmitted from the black-and-white scan converter 301 and the video signal representative of the M-mode image transmitted from the scroll scan converter 303 are arranged side by side, and in addition a function such that a color mode image, which will be described later, is superposed on the B-mode image. The observation television monitor 707 is adapted to display thereon a plurality of images being arranged side by side in accordance with an instruction from an operator, alternatively display a plurality of images being superposed.

Again, returning to the explanation of the analog processing unit 200, the Doppler signal processing unit 206, which constitutes the analog processing unit 200, serves as a structure element for determining a blood flow distribution of the inside of the subject, or a blood flow distribution at a certain point or on a certain one scanning line. In the Doppler signal processing unit 206, a signal representative of the received ultrasonic beam generated in the beamformer unit 203 is subjected to a so-called quadrature detection and in addition converted into digital data through an A/D conversion. The data, which has been subjected to the quadrature detection, is outputted from the Doppler signal processing unit 206, is fed to the Doppler processing unit 400. The Doppler processing unit 400 comprises the pulse/continuous wave Doppler analyzing unit 401 and the color Doppler analyzing unit 402. Here, it is assumed that the data outputted from the Doppler signal processing unit 206 is fed to the color Doppler analyzing unit 402. The color Doppler analyzing unit 402 determines data representative of a blood flow distribution on an area of interest (ROI) on the B-mode image, which is designated by an operator, by an auto-correlation operation based on data obtained through performing, for example, eight times of ultrasonic transmit and receive on each scan line. The data representative of a blood flow distribution on the area (ROI) is fed via the echo bus 902 to the color scan converter 302. The color scan converter 302 converts the data representative of a blood flow distribution on the area (ROI) into a video signal suitable for a display, and transmits the video signal to the display control unit 500. The display control unit 500 superimposes a color mode image, in which a blood in a direction coming near the ultrasonic probe 20, a blood in a direction going away from the ultrasonic probe 20, and a blood velocity are represented by, for example, red, blue and luminance, respectively, on the area (ROI) of the B-mode image transmitted from the black-and-white scan converter 301, and causes those images to be displayed on the observation television monitor 707. Thus, it is possible to grasp the outline of the blood flow distribution on the area (ROI).

When an operator inputs a requirement to observe in detail a blood at a certain one point on the area (ROI) or on a certain one scanning line, then the transmit-receive unit 201 repeats a lot of number of times of transmit and receive of the ultrasonic waves in a direction along a one scan line passing through the one point, or a direction along the one scanning line of interest. And data, which is generated in the Doppler signal processing unit 206 in accordance with the signals thus obtained by the repetitive transmit and receive of the ultrasonic waves, is fed to the pulse/continuous wave Doppler analyzing unit 401 constituting the Doppler processing unit 400. When it is interested in the a blood flow at a certain point, a pulse-like shaped ultrasonic beam is transmitted into the subject. On the other hand, when it is desired to obtain blood information excellent in S/N ratio, permitting that blood information on a certain one scan line is averaged, a ultrasonic beam is transmitted in the form of a continuous wave into the subject.

The pulse/continuous wave Doppler analyzing unit 401 performs an FFT (Fast Fourier Transform) operation based on data obtained through carrying out a lot of number of times of transmit and receive of the ultrasonic waves on a certain one point, or a certain one scanning line to obtain blood flow information on the one point, or blood flow information averaged on the one scanning line. Data representative of the blood flow information obtained in the pulse/continuous wave Doppler analyzing unit 401 is fed via the echo bus 902 to the scroll scan converter 303. The scroll scan converter 303 generates a video signal representative of an image in which the longitudinal axis and the lateral axis denote a blood flow velocity and a time axis, respectively, and the image may scroll in a direction of the time axis. This video signal is fed via the video bus 903 to the display control unit 500. The display control unit 500 causes the video signal to be displayed on the observation television monitor 707 together with the B-mode image transmitted from the black-and-white scan converter 301, for example.

Figure 2:
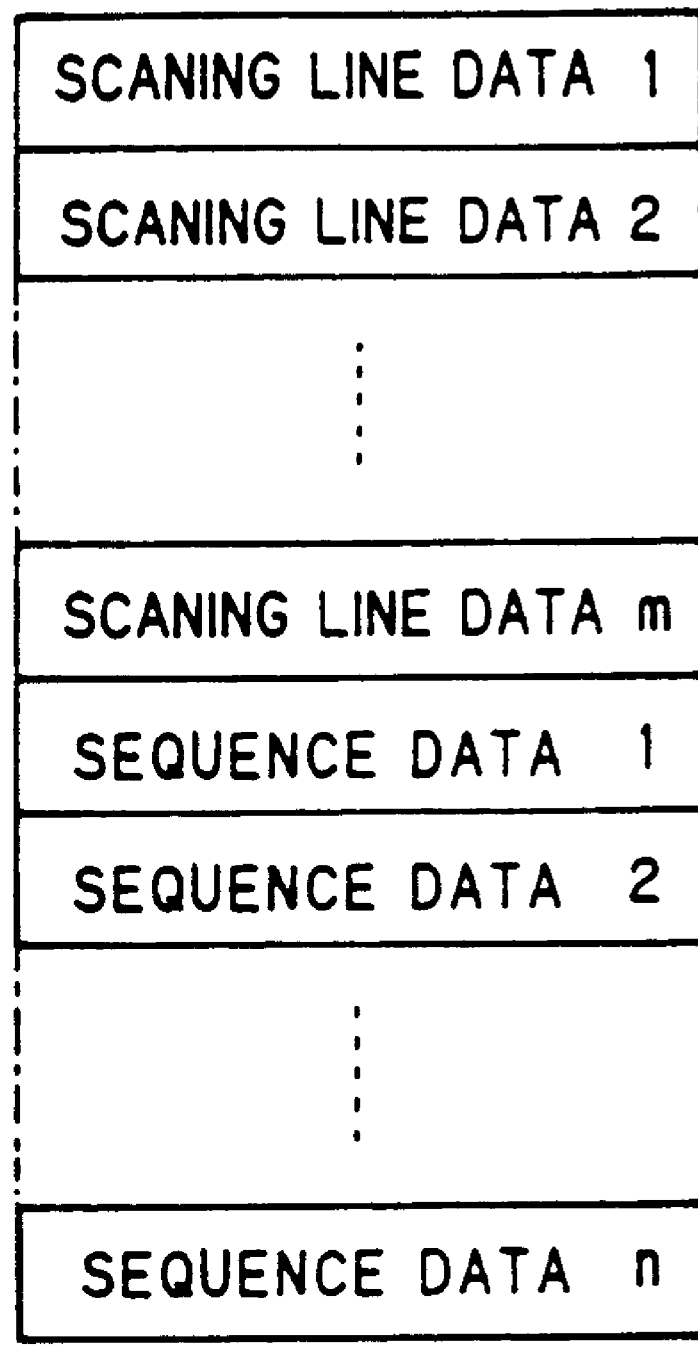
FIG. 2 is a conceptual view of data stored in a transmit-and-receive memory shown in FIG. 1 with a one block.

FIG. 2 is a conceptual view of data stored in the transmit-and-receive memory 103 shown in FIG. 1 with a one block.

The transmit-and-receive memory stores therein a lot of scanning line data 1-m, and a lot of sequence data 1-n. Each of the scanning line data comprises a set of data defining attributes of transmitting ultrasonic beams and received ultrasonic beams along a certain scanning line as to a certain ultrasonic probe. Specifically, a certain scanning line data (e.g. scanning line data 1) is suitable for a certain specific type of ultrasonic probe, and consists of a set of data for defining relative time differences (the relative time differences are referred to as a delay pattern in their entirety) of high voltage pulses, which are applied to the plurality of ultrasonic transducers 211, respectively, to form a transmitting ultrasonic beam having a certain frequency, transmitted in a direction along a certain one scanning line of a plurality of scanning lines 2 as to the ultrasonic probe 20, a focus of which transmitting ultrasonic beam is formed at a certain depth position, and for defining pulse width and repetitive period of the high voltage pulses, which are applied to the plurality of ultrasonic transducers 211, respectively, and additional data for defining relative delay times (the relative delay times are also referred to as a delay pattern in their entirety) of received signals obtained in the plurality of ultrasonic transducers 211 to define a direction and a focus of a received ultrasonic beam.

Each of the sequence data, for example, sequence data 1, is for defining a sequence of reading of scanning line data. A plurality of scanning line data are sequentially read in accordance with a sequence determined by the sequence data, so that the transmit-and-receive of ultrasonic beams are sequentially performed in accordance with the sequence data thus read out. Specifically, when it is indicated that a certain ultrasonic probe is used through an operation of the handler 7011, and a transmit-receive mode, which will be described later, is selected, then a suitable sequence data is read from the transmit-and-receive memory 103 by the beam scan control unit 102. To transmit and receive ultrasonic waves, the beam scan control unit 102 first reads scanning line data for performing transmission and reception of ultrasonic beams along the scanning line of the most left end of the plurality of scanning lines 2 shown in FIG. 1, for example, in accordance with the sequence data thus read, and transmits the scanning line data thus read to the analog processing unit 200 wherein the transmission and reception of the ultrasonic beams along the scanning line are performed, and the beam scan control unit 102 next reads scanning line data for performing transmission and reception of ultrasonic beams along the second scanning line from the most left end of the plurality of scanning lines 2 shown in FIG. 1, and transmits the scanning line data thus read to the analog processing unit 200 wherein the transmission and reception of the ultrasonic beams along the scanning line are performed. In a similar fashion to that of the above, the transmission and reception of ultrasonic beams along the subsequent scanning lines are performed in turn, and finally the transmission and reception of ultrasonic beams along the most right end scanning line is performed, whereby a frame of received signals are obtained, so that a sheet of image on the scanning area 3 is produced. Subsequently, in order to produce the next frame of image, the routine returns to the transmission and reception of ultrasonic beams along the scanning line of the most left end.

FIG. 3 is a conceptual view showing delay patterns of high voltage pulses to be applied to a plurality of ultrasonic transducers.

High voltage pulses 212 are applied to a plurality of ultrasonic transducers 211 arranged with greater delay as the ultrasonic transducers 211 are located at the position closer to the center (part (0) of FIG. 3) of the arrangement as compared with both ends (parts (A) and (B) of FIG. 3) of the arrangement. In this manner, an application of the high voltage pulses having the delay patterns to the ultrasonic transducers 211 makes it possible to form transmit-receive ultrasonic pulse beams extending in a predetermined direction within the subject and having a focus formed at a certain depth position.

FIGS. 4(A) and 4(B) are typical illustrations each a state in which a high voltage pulse train having different pulse width and repetitive period is applied to an ultrasonic transducer.

In the comparison of FIG. 4(A) with FIG. 4(B), it will be understood that in FIG. 4(B) rather than FIG. 4(A), a high voltage pulse train having wider pulse width and longer repetitive period is applied to an ultrasonic transducer 211.

In order to obtain a larger variation of frequency of the ultrasonic waves for use in transmit-and-receive, there is a need to prepare an ultrasonic probe, in which ultrasonic transducers suitable for the associated frequency are arranged, for each frequency. As shown in FIGS. 4(A) and 4(B), however, a control of the pulse width and the repetitive period of the high voltage pulses to be applied to the ultrasonic transducer 211 makes it possible to control the frequency of the ultrasonic waves within a certain limit.

FIG. 5 is a diagram used for the explanation of the principle of a formation of a received ultrasonic beam in the beamformer.

Here, for the purpose of simplification of the explanation, it is assumed that the respective pairs of delay lines 1001a, . . . , 1001m, . . . , and 1001n each having a plurality of taps, and selection switches 1002a, . . . , 1002m, . . . , and 1002n each for selecting an input route of a received signal to a delay line according to a control signal are provided for the associated ultrasonic transducers 211, respectively. Each of the selection switches 1002a, . . . , 1002m, . . . , and 1002n receives a one received signal obtained in an associated one ultrasonic transducer 211. In each of the selection switches 1002a, . . . , 1002m, . . . , and 1002n, the input received signal is fed to an associated delay line through a tap according to a control signal, of a plurality of taps of the delay line. In each of the delay lines 1001a, . . . , 1001m, . . . , and 1001n, the received signal is delayed by a delay time according to the tap to which the received signal is fed, and the received signal thus delayed is applied to an adder 1003. The adder 1003 adds the received signals, which are simultaneously applied thereto, and outputs a scanning line signal representative of a received ultrasonic beam.

Incidentally, it is to be noted that in FIG. 5, for the purpose of the easier understanding of the present invention, there is shown an arrangement in which the respective pairs of delay lines 1001a, . . . , 1001m, . . . , and 1001n and selection switches 1002a, . . . , 1002m, . . . , and 1002n, the number of which pairs is equal to that of the ultrasonic transducers, are provided and further the adder 1003 for adding the received signals together, which are outputted from the delay lines 1001a, . . . , 1001m, . . . , and 1001n, is provided. Indeed, however, a plurality of received signals, which are obtained in a plurality of ultrasonic transducers, are inputted into a single delay line having a number of taps, while the taps to which the received signals are applied, respectively, are controlled, so that the plurality of received signals are delayed by the times associated taps, respectively, and then added to each other in the delay line on a current basis. In this manner, a scanning line signal, which is subjected to a delay according to the controlled delay pattern and also an addition, or a so-called beamformation, is directly outputted from the single delay line.

FIGS. 6(A), 6(B) and 6(C) are explanatory views each showing a relationship among a delay pattern, a direction of a scanning line and a point of a focus.

In each of FIGS. 6(A), 6(B) and 6(C), it is assumed that a plurality of ultrasonic transducers are arranged between points A and B, and an intermediate point between the points A and B is denoted by a point 0. At that time, as shown in FIG. 6(A), when high voltage pulses are applied to the ultrasonic transducers in such a manner that rather longer delay time is given for the ultrasonic transducers located at the point B side, there will be formed a transmission ultrasonic beam along a scanning line extending in a direction leaning to the point B side with respect to the intermediate point 0. As shown in FIG. 6(B), when high voltage pulses are applied to the ultrasonic transducers with a symmetrical delay pattern with respect to the intermediate point 0 between points A and B, there will be formed a transmission ultrasonic beam along a scanning line extending perpendicularly to an arrangement direction of the ultrasonic transducers with respect to the intermediate point 0. As shown in FIG. 6(C), when high voltage pulses are applied to the ultrasonic transducers in such a manner that rather longer delay time is given for the ultrasonic transducers located at the point A side, there will be formed a transmission ultrasonic beam along a scanning line extending in a direction leaning to the point A side with respect to the intermediate point 0. Further, even if the transmission ultrasonic beams along the same scanning line are concerned, it is possible to determine the focus point in accordance with a delay pattern of the high voltage pulses to be applied to the ultrasonic transducers. Specifically, as shown in each of FIGS. 6(A), 6(B) and 6(C) with a broken line, let us consider such a situation that a circle arc, which is in contact with a segment coupling between the points A and B, is drawn with the focus as the central part. When ultrasonic pulses transmitted from the respective ultrasonic transducers reach simultaneously on the circular arc, the ultrasonic pulses travel so as to gather to the focus. Therefore, for example, in the event that the focus is formed as shown in FIG. 6(B), high voltage pulses are simultaneously applied to the ultrasonic transducers located at the points A and B, so that the ultrasonic transducers simultaneously generate ultrasonic pulses, respectively. And a high voltage pulse is applied to an ultrasonic transducer located at the point 0 at the timing that the ultrasonic pulses, which are generated from the ultrasonic transducers located at the points A and B, reach the circular arc, so that the ultrasonic transducer located at the point 0 generates ultrasonic pulse. In this manner, it is possible to form a transmission ultrasonic pulse beam along the scanning line shown in FIG. 6(B) and having the narrowest beam diameter at the focus point shown in FIG. 6(B).

It is to be noted that the plurality of ultrasonic transducers used for the ultrasonic transmission, which are arranged between the points A and B, are, for example, part of the plurality of ultrasonic transducers 211 arranged in the ultrasonic probe 20 (cf. FIG. 1), and a movement of a transmission aperture, which consists of the plurality of ultrasonic transducers for use in a formation of the transmission ultrasonic pulse beam, in an arrangement direction of the ultrasonic transducers 211 arranged in the ultrasonic probe 20, makes it possible to shift the scanning line in parallel with respect to the arrangement direction of the ultrasonic transducers 211. In case of the ultrasonic probe 20 shown in FIG. 1, however, since the ultrasonic transducers 211 are arranged as a circular arc, the scanning line moves to draw a circular arc, but not a parallel movement.

In this manner, it is possible to obtain a transmission ultrasonic beam travelling along a scanning line extending in an arbitrary direction within the subject taking as a starting point an arbitrary point on the ultrasonic transducers 211 arranged on the ultrasonic probe 20, and having a focus on an arbitrary point on the scanning line.

Also with respect to the formation of received ultrasonic beams, it is similar to that of the above-mentioned transmission ultrasonic beam.

That is, with respect to received signals obtained by receiving ultrasonic waves reflected within the subject and returned to the ultrasonic transducers, as shown in FIG. 6(A), when rather longer delay time is given for received signals obtained by ultrasonic transducers located at the point B side, and then the received signals are added to each other, there will be formed a received ultrasonic beam along a scanning line leaning to the point B side with respect to the intermediate point 0. As shown in FIG. 6(B), when a symmetrical delay time is given for received signals obtained by the ultrasonic transducers, and then the received signals are added to each other, there will be formed a received ultrasonic beam along a scanning line extending perpendicularly to an arrangement direction of the ultrasonic transducers with respect to the intermediate point 0. As shown in FIG. 6(C), when rather longer delay time is given for received signals obtained by ultrasonic transducers located at the point A side, and then the received signals are added to each other, there will be formed a received ultrasonic beam along a scanning line leaning to the point A side with respect to the intermediate point 0. Further, even if the received ultrasonic beams along the same scanning line are concerned, it is possible to determine the focus point in accordance with a delay pattern. Specifically, as shown in each of FIGS. 6(A), 6(B) and 6(C), ultrasonic waves reflected on the focus and directed toward the points A, 0 and B, respectively, arrive simultaneously at cross points of the segments coupling the focus with the points A, 0 and B, respectively and the circular arc shown with a broken line, and thus there will occur a difference in time of receiving of the ultrasonic waves reflected on the focus by the respective ultrasonic transducers. Thus, the received signals, which are derived in the ultrasonic transducers at which the ultrasonic waves reflected on the focus arrive earlier, are delayed until ultrasonic waves arrive at the ultrasonic transducers at which the ultrasonic waves arrive with a delay, and then added to each other. In this manner, it is possible to form a received ultrasonic beam extending in a direction along the scanning line passing through the focus and having the narrowest beam diameter at the focus point.

It is to be noted, in a similar fashion to that of the transmission, that the plurality of ultrasonic transducers used for the reception of the reflected ultrasonic waves, which are arranged between the points A and B, are, for example, part of the plurality of ultrasonic transducers 211 arranged in the ultrasonic probe 20 (cf. FIG. 1), and a movement of a reception aperture, which consists of the plurality of ultrasonic transducers for use in a reception of the reflected ultrasonic waves, in an arrangement direction of the ultrasonic transducers 211 arranged in the ultrasonic probe 20, makes it possible to shift the scanning line in parallel with respect to the arrangement direction of the ultrasonic transducers 211. In case of the ultrasonic probe 20 shown in FIG. 1, however, since the ultrasonic transducers 211 are arranged as a circular arc, the scanning line moves to draw a circular arc, but not a parallel movement, similar to the case of the transmission.

In this manner, with respect to both the transmission and the reception, it is possible to obtain an ultrasonic beam travelling along a scanning line extending in an arbitrary direction within the subject taking as a starting point an arbitrary point on the ultrasonic transducers 211 arranged on the ultrasonic probe 20, and having a focus on an arbitrary point on the scanning line.

The above-mentioned matter is concerned with the explanation as to the outline of the ultrasonic diagnostic apparatus according to the embodiment of the present invention. Next, there will be described the more essential details of the present embodiment, hereinafter.

In case of the embodiment shown in FIG. 1, as will be apparent from the following description, the combination of the whole of the analog processing unit 200, but not the transmit-receive unit 201 only, the Doppler processing unit 400, and functions of controlling the analog processing unit 200 and the Doppler processing unit 400, of the control unit 100, corresponds to the transmit-receive unit referred to in the present invention. And the combination of the digital scan converter unit 300, the display control unit 500, a function of producing a graphic image, of the CPU unit 101, and functions of controlling the digital scan converter unit 300 and the display control unit 500, of the control unit 100, and in addition the combination of the printer 705, the VTR 706 and the observation TV monitor 707, corresponds to the image producing unit referred to in the present invention.

Figure 7A:
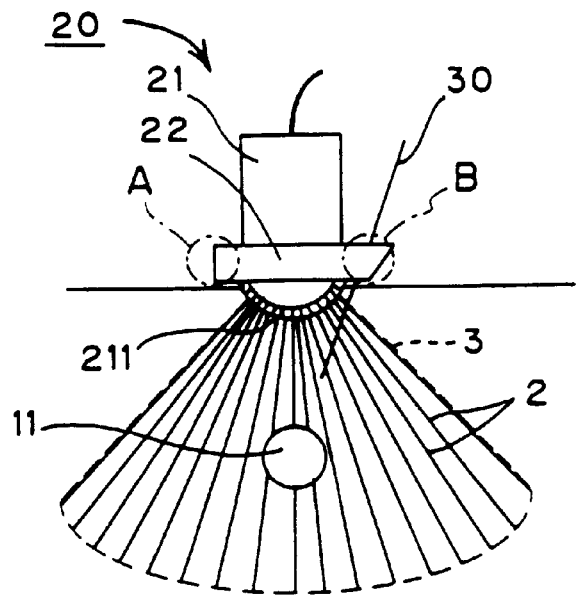
FIGS. 7(A), 7(B) and 7(C) are typical illustrations each showing an example of scanning of the inside of the subject by ultrasonic waves.
Figure 7B:
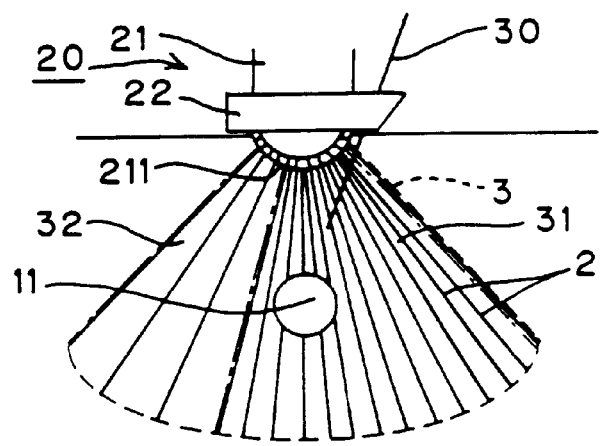
Figure 7C:
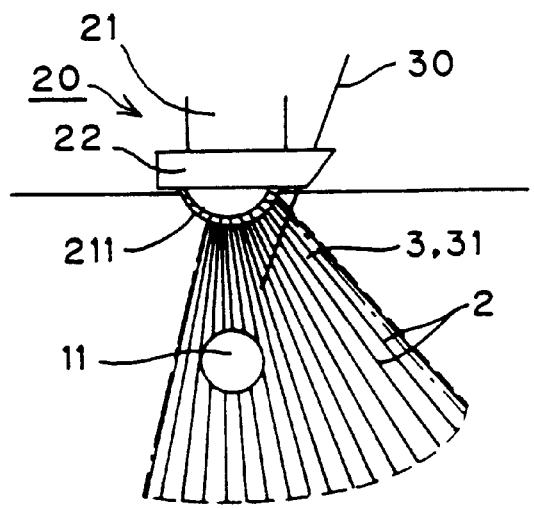

FIGS. 7(A), 7(B) and 7(C) are typical illustrations each showing an example of scanning of the inside of the subject by ultrasonic waves.

According to the example shown in FIG. 7(A), similar to the example shown in FIG. 21, a plurality of scanning lines 2 are spread uniformly within the scanning area 3. This example corresponds to an example of a first transmit-receive mode referred to in the present invention. Incidentally, with respect to the point that circles A and B are added in FIG. 7(A), it will be described later.

According to the example shown in FIG. 7(B), there is shown a state that, of the scanning area 3, a first area 31 including the passage area of the puncture needle 30 is scanned with a higher density of scanning line than a second area 32 except the first area 31, of the scanning area 3. This example corresponds to an example of a second transmit-receive mode referred to in the present invention, or a second transmit-receive mode referred to in the first ultrasonic diagnostic apparatus according to the present invention.

According to the example shown in FIG. 7(C), there is shown a state that the scanning area 3 itself is narrowed to the same area as the first area 31 shown in FIG. 7(B), and the scanning is performed on the first area 31 consisting of the narrowed scanning area 3. This example also corresponds to an example of the second transmit-receive mode referred to in the present invention, or a second transmit-receive mode referred to in the second ultrasonic diagnostic apparatus according to the present invention.

A selection of these modes is performed in such a manner that sequence data (cf. FIG. 2) corresponding to the modes are stored in the transmit-receive memory 103 and the handler 7013 of the control panel is operated. When the handler 7013 is operated to select anyone of the transmit-receive modes, the beam scan control unit 102 reads from the transmit-receive memory 103 the sequence data associated with the transmit-receive mode designated by an operation of the handler 7013, and sequentially reads the scanning line data (cf. FIG. 2), which are stored in the transmit-receive memory 103, in accordance with the sequence data thus read out, thereby implementing the selected transmit-receive mode for transmission and reception of ultrasonic waves.

Figure 8:
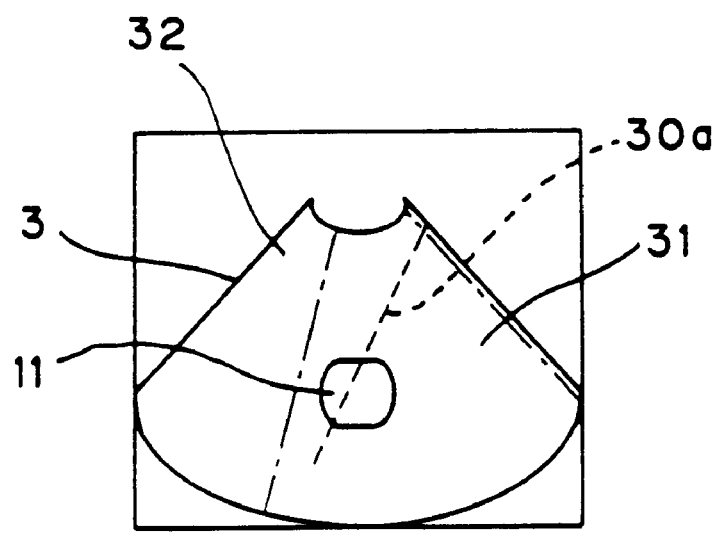
FIG. 8 is a typical illustration of an example of an image displayed on the observation TV monitor shown in FIG. 1.

FIG. 8 is a typical illustration of an example of an image displayed on the observation TV monitor 707 shown in FIG. 1.

In the mode of FIG. 7(A), images of the whole area of the broad scanning area 3 are displayed with a homogeneous resolution on the observation TV monitor 707. In the mode of FIG. 7(B), while the broad scanning area 3 is ensured, images are displayed on the observation TV monitor 707 with a high resolution as to the first area 31 and a low resolution as to the second area 32, respectively. In the mode of FIG. 7(C), images are displayed with respect to the scanning area which is the same as the first area 31, that is, the narrow scanning area.

According to the example shown in FIG. 8, there is also displayed a diagram 30*a* representative of the passage of the puncture needle. It is selected by the handler 7014 of the control panel 701 shown in FIG. 1 as to whether the diagram 30*a* is displayed. When it is instructed that the diagram 30*a* is displayed, the CPU 101 generates the diagram 30*a* and transmits the same via the CPU bus 901 to the display control unit 500. In the display control unit 500, the diagram 30*a* is superimposed on the B-mode image which is produced in the black-and-white scan converter 301 and transferred via the video bus 903 to the display control unit 500.

While it has been described above that the selection among the transmit-receive modes of FIGS. 7(A), 7(B) and 7(C) is performed by the handler 7013, and the selection between the display and the non-display of the diagram 30*a* shown in FIG. 8 is performed by the handler 7014, it is acceptable that these handlers are used on a common basis, for example, in such a manner that in case of the transmit-receive mode of FIG. 7(A), the diagram 30*a* is not displayed, alternatively, in case of the transmit-receive mode of FIGS. 7(B) or 7(C), the diagram 30*a* is displayed. This scheme makes it impossible to perform independently the selection among the transmit-receive modes and the selection between the display and the non-display of the diagram, but makes it possible to improve the operability.

When the diseased part 11 is simply observed, the mode of FIG. 7(A) is adopted so that a broad scanning area is ensured and a predetermined homogeneous resolution can be obtained throughout the broad scanning area. Alternatively, when the puncture needle 30 is introduced into the diseased part 11, the mode of FIGS. 7(B) or 7(C) is adopted so that a high resolution of image can be obtained with respect to an area including the passage of the puncture needle 30. The mode of FIG. 7(B) has an advantage such that a broad scanning line area can be ensured. On the other hand, the mode of FIG. 7(C) has an advantage such that while the scanning line area is narrowed as compared with the mode of FIG. 7(B), the corresponding frame rate can be enhanced.

Figure 9:
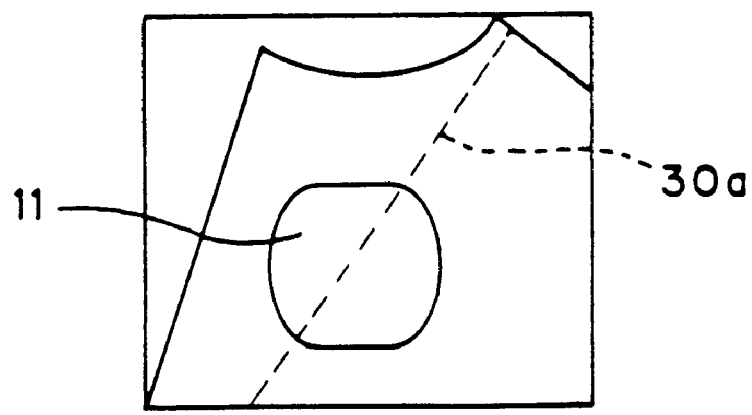
FIG. 9 is a typical illustration of an alternative example of an image displayed on the observation TV monitor shown in FIG. 1.

FIG. 9 is a typical illustration of an alternative example of an image displayed on the observation TV monitor 707 shown in FIG. 1.

In FIG. 9, there is shown an enlarged image representative of an area (enlarged area) surrounding the diseased part 11.

To display the enlarged image as shown in FIG. 9 on the observation TV monitor 707, the handler 7015 on the control panel 701 shown in FIG. 1 is operated, at the stage that the whole image as shown in FIG. 8 is displayed, to designate a region of interest (ROI) to be enlarged and instruct it to be enlarged. Then, position information of the enlarged area is fed from the CPU 101 via the CPU bus 901 to the black-and-white scan converter 301. In the black-and-white scan converter 301, an interpolation processing is performed to obtain an enlarged image on the enlarged area, so that an image representative of the enlarged area only is produced. When the diagram 30*a* is superimposed on the image thus produced, the CPU 101 produces a diagram suitable for the enlarged area.

A combination of a production of such an enlarged image and the transmit-receive mode of FIG. 7(C) for example serves to improve the resolution and also to display the enlarged image thereby obtaining an image more preferable for the puncture technology.

Incidentally, while the diagram 30*a* is shown also in the enlarged image shown in FIG. 9, it is acceptable to provide such an arrangement that the mode wherein the enlarged image is produced and displayed, and the mode wherein the diagram 30*a* is displayed, are combined with each other, and the handler 7014 for selecting whether the diagram 30*a* is displayed and the handler 7015 for designating an image enlargement are used on a common basis, for example, in such a manner that when the usual size of image is displayed, the diagram 30*a* is not displayed, and the when the enlarged image is displayed, the diagram 30*a* is displayed. This scheme makes it impossible to perform independently the selection between the image producing modes and the selection between the display and the non-display of the diagram, but makes it possible to save one trouble for the operation by the corresponding.

FIGS. 10(A) and 10(B) are typical illustrations each showing an example of an internal structure of a portion encircled by a circle A shown in FIG. 7(A).

At the main frame 21 side of the ultrasonic probe, there are provided two fixed contacts 21*a*__1 and 21*a*__2, a single movable contact 21*b*, and a detector 21*c* for detecting whether the two fixed contacts 21*a*__1 and 21*a*__2 conduct with each other through the movable contact 21*b*.

FIG. 10(A) shows the state that the guide member 22 is not loaded onto the main frame 21 side of the ultrasonic probe, in which the two fixed contacts 21*a*__1 and 21*a*__2 do not conduct with each other. FIG. 10(B) shows the state that the guide member 22 is loaded onto the main frame 21 side of the ultrasonic probe, in which the movable contact 21*b* is urged by the projection 22*b* of the guide member 22 so that the two fixed contacts 21*a*__1 and 21*a*__2 conduct with each other. The state of the conduction or the non-conduction between the two fixed contacts 21*a*__1 and 21*a*__2 is detected by the detector 21*c*. Information as to the detected result is transferred through the transmit-receive unit 201, the control line 207, the control interface unit 204 and the CPU bus 901 to the CPU 101 and the beam scan control unit 102. In the CPU 101, information as to whether the guide member 22 is loaded onto the main frame 21 of the ultrasonic probe is used for the purpose of generation of diagram 30*a* representative of the passage of the puncture needle, as shown in FIG. 8 and FIG. 9, and also for the purpose of displaying on an image screen the fact that the guide member 22 is loaded onto the main frame 21 of the ultrasonic probe. Also in the beam scan control unit 102, such information is used for a selection among the transmit-receive modes (cf. FIGS. 7(A), 7(B) and 7(C)).

Figure 10:
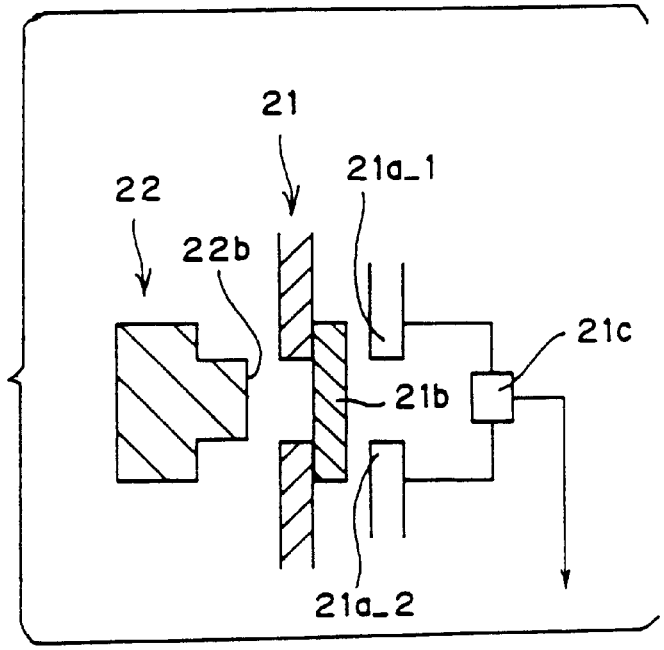
FIGS. 10(A) and 10(B) are typical illustrations each showing an example of an internal structure of a portion encircled by a circle A shown in FIG. 7(A)
Figure 10:
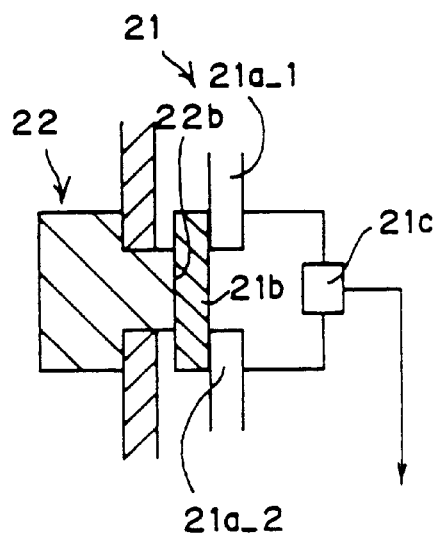

Specifically, according to the present embodiment, as shown in FIGS. 10(A) and 10(B), there is provided a sensor or a detector for detecting a loading of the guide member 22 onto the main frame 21. And instead of providing the handler 7013 for selection among the transmit-receive modes as in FIGS. 7(A), 7(B) and 7(C)), the sensor is used, when it is detected that the guide member 22 is not loaded onto the main frame 21, to select the transmit-receive mode as shown in FIG. 7(A), alternatively when it is detected that the guide member 22 is loaded onto the main frame 21, to select the transmit-receive mode as shown in FIGS. 7(B) and 7(C). It is acceptable that both the handler 7013 and the sensor as shown in FIG. 10 are provided, and also acceptable that an additional handler 7016 is provided to optionally select an mode between a manual mode in which the handler 7013 is effective and an automatic mode in which the sensor as shown in FIG. 10 is effective.

Further, it is acceptable that instead of providing the handler 7015 for selection as to whether the usual size of image is to be produced and displayed, or an enlarged image is to be produced and displayed, the above-mentioned sensor is used, when it is detected that the guide member 22 is not loaded onto the main frame 21, to produce the image to be displayed throughout the scanning line area 3 as shown in FIG. 8 (or to select the first image producing mode referred to in the present invention), alternatively when it is detected that the guide member 22 is loaded onto the main frame 21, to produce the enlarged image as shown in FIG. 9 (or to select the second image producing mode referred to in the present invention). It is acceptable that both the handler 7015 and the sensor as shown in FIG. 10 are provided, and also acceptable that the additional handler 7016 is provided to optionally select an mode between a manual mode in which the handler 7015 is effective and an automatic mode in which the sensor as shown in FIG. 10 is effective. In this manner, also with respect to the production of the enlarged image, it is acceptable to use the the manual mode and the automatic mode appropriately.

Figure 11:
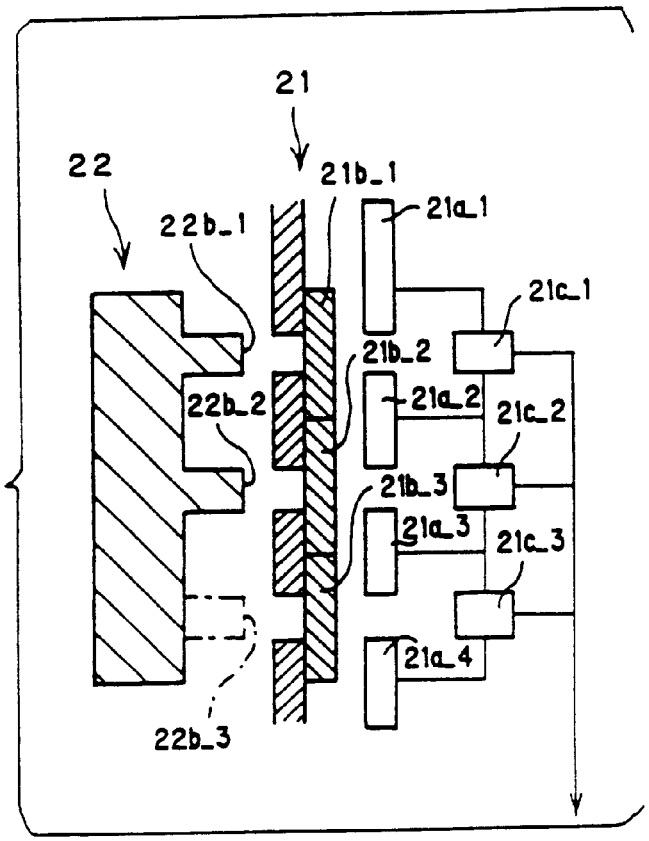
FIGS. 11(A) and 11(B) are typical illustrations each showing an alternative example of an internal structure of a portion encircled by a circle A shown in FIG. 7(A)
Figure 11:
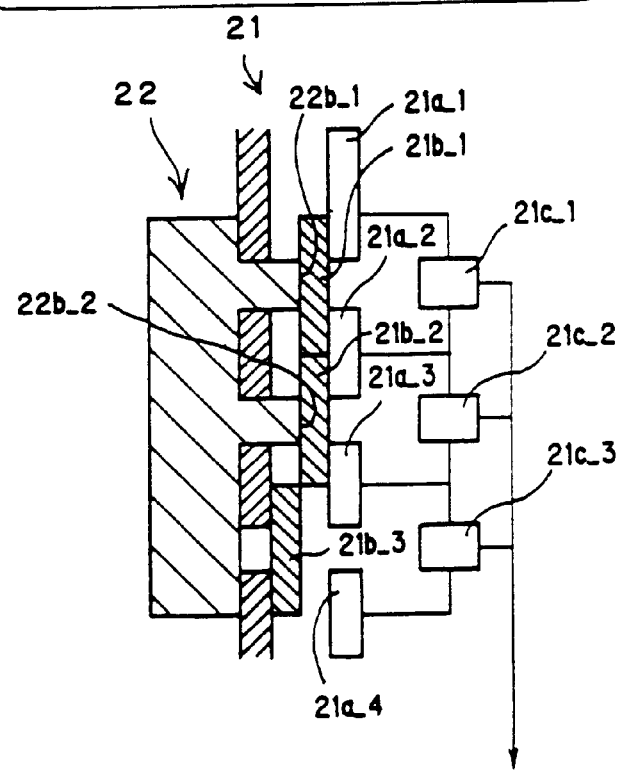

FIGS. 11(A) and 11(B) are typical illustrations each showing an alternative example of an internal structure of a portion encircled by a circle A shown in FIG. 7(A).

At the main frame 21 side of the ultrasonic probe, there are provided four fixed contacts 21a_1, 21a_2, 21a_3 and 21a_4, three movable contacts 21b_1, 21b_2 and 21b_3, and three detectors 21c_1, 21c_2 and 21c_3 for detecting whether the pairs of the fixed contacts 21a_1 and 21a_2; the fixed contacts 21a_2 and 21a_3; and the fixed contacts 21a_3 and 21a_4 conduct with each other, respectively.

At the guide member 22 side, there are provided the maximum 3 projections 22b_1, 22b_2 and 22b_3 according to types of the guide member. In case of the guide member 22 shown in FIGS. 11(A) and 11(B), there are provided two projections 22b_1 and 22b_2.

FIG. 11(A) shows the state that the guide member 22 is not loaded onto the main frame 21 side of the ultrasonic probe, in which the pairs of the fixed contacts 21a_1 and 21a_2; the fixed contacts 21a_2 and 21a_3; and the fixed contacts 21a_3 and 21a_4 do not conduct with each other. FIG. 11(B) shows the state that the guide member 22 is loaded onto the main frame 21 side of the ultrasonic probe, in which anyone or two or more of the pairs of the fixed contacts 21a_1 and 21a_2; the fixed contacts 21a_2 and 21a_3; and the fixed contacts 21a_3 and 21a_4 conduct with each other in accordance with types of the guide member. According to the example shown in FIG. 11(B), the pair of the fixed contacts 21a_1 and 21a_2 conducts through the movable contacts 21b_1, and the pair of the fixed contacts 21a_2 and 21a_3 conducts through the movable contacts 21b_2. And the pair of the fixed contacts 21a_3 and 21a_4 is kept on a non-conduction state. The state of the conduction or the non-conduction of the respective pairs of the fixed contacts is detected by the detectors 21c_1, 21c_2 and 21c_3. Information obtained by such a detection includes information as to whether the guide member 22 is loaded onto the main frame 21 side of the ultrasonic probe, and in addition, when the guide member 22 is loaded onto the main frame 21, information indicative of a type of the guide member loaded.

The information as to the detected result is transferred to the CPU 101 and the beam scan control unit 102, in a similar fashion to that of the example shown in FIGS. 10(A) and 10(B).

A type of the guide member 22 is concerned with a difference of an angle of guiding a puncture needle. That is, according as there is a need to introduce the puncture needle a shallow portion of the subject or a deep portion of the subject, a different type of guide member 22 is loaded onto the main frame 21.

Consequently, a position and an angle of the diagram 30a, which is representative of the passage of the puncture needle as shown in FIG. 8 and FIG. 9, on the image screen, is varied in accordance with a type of the guide member loaded onto the main frame 21 of the ultrasonic probe, so that the CPU 101 produces the diagram according to the guide member loaded. Since the region on the image screen, in which the puncture needle 30 is introduced, is varied in accordance with a type of the guide member, it happens that the region (the first area 31) shown in FIGS. 7(B) and 7(C), which is concerned with an improvement of the resolution, is varied in accordance with a type of the guide member, and then the beam scan control unit 102 provides such a control that the first area 31 shown in FIGS. 7(B) and 7(C) changes over in accordance with a type of the guide member loaded onto the main frame 21 of the ultrasonic probe. This change over is performed, as mentioned above, by means of reading from the transmit-and-receive memory 103 different sequence data.

Also with respect to the generation of the enlarged image, in a similar fashion to that of the change over of the transmit-receive mode, the region of interest (ROI) is automatically altered so that the region including the passage of the puncture needle introduced through the guide member is enlarged in accordance with a type of the guide member loaded. In this case, it is acceptable that the function of the designation of the ROI is removed from the handler 7015 so that the handler 7015 serves as an handler for designating only whether an enlarged image is to be generated. Alternatively, it is acceptable that it is selected, by an operation of the handler 7016 for optionally selecting an mode between a manual mode and an automatic mode, as to whether the designation of the ROI is to be performed through the handler 7015 or in accordance with information generated from the sensors shown in FIGS. 11(A) and 11(B).

Figure 12:
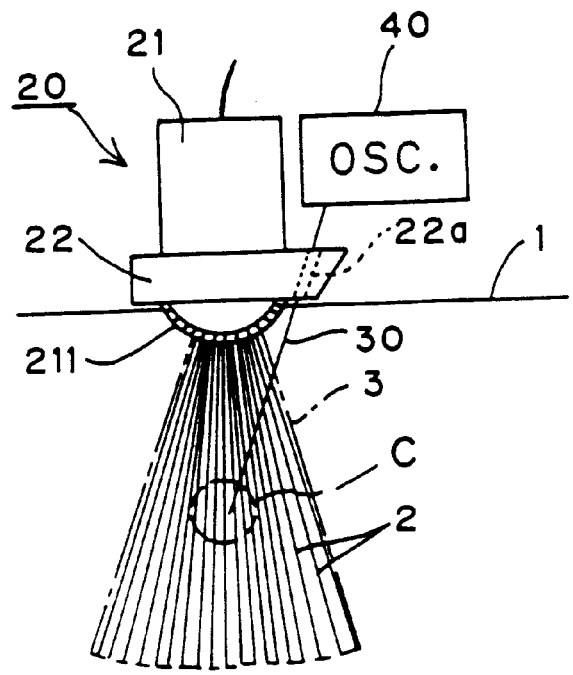
FIG. 12 is a typical illustration of the tip portion of the ultrasonic probe.
Figure 13:
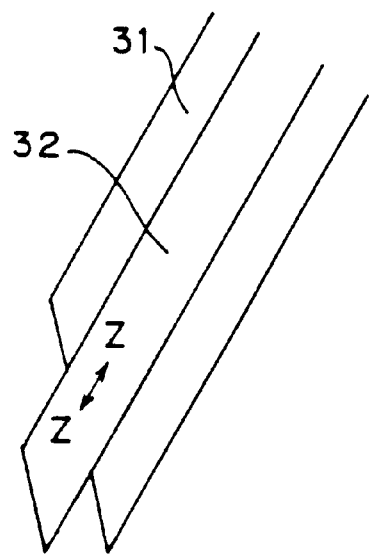
FIG. 13 is an expanded sectional view of the tip portion of a puncture needle 30 shown in FIG. 12 with a circle C.

FIG. 12 is a typical illustration of the tip portion of the ultrasonic probe. FIG. 13 is an expanded sectional view of the tip portion of a puncture needle 30 shown in FIG. 12 with a circle C.

The puncture needle 30 comprises a hollow needle 31 and an inner needle 32 slidably contacted with an inner wall of the hollow needle 31. On a one edge portion of the puncture needle 30, as shown in FIG. 12, there is provided an oscillator 40 for vibrating the inner needle 32 of the puncture needle 30 in the longitudinal direction (an arrow Z—Z direction shown in FIG. 13). When the oscillator 40 applies vibrations to the inner needle 32, ultrasonic waves, which are transmitted from the ultrasonic transducers 211 of the ultrasonic probe 20 and reflected on the tip portion of the inner needle 32, are subjected to a Doppler transition owing to vibrations of the inner needle 32. The ultrasonic waves, which are reflected on the tip portion of the inner needle 32, while being subjected to a Doppler transition, and return to the ultrasonic transducers 211, are received by the ultrasonic transducers 211 in a similar fashion to that of ultrasonic waves reflected on other tissues within the subject and returned to the ultrasonic transducers 211. The ultrasonic waves thus received are transferred via the transmit-receive unit 201, the beamformer unit 203 and the Doppler signal processing unit 206 to the color Doppler analyzing unit 402, although it is not concerned with the color display of the blood flow. The color Doppler analyzing unit 402 performs the same operation as that of evaluating the blood flow distribution to detect a point on which the ultrasonic waves are subjected to the Doppler transition, that is, the tip position of the puncture needle 30. Information representative of the tip position of the puncture needle 30 is fed via the CPU bus 901 to the beam scan control unit 102. The beam scan control unit 102 determines the first area 31 shown in FIGS. 7(B) and 7(C) in accordance with the position of the tip of the puncture needle 30 so that the area near the tip of the puncture needle 30 is of a high resolution of image. Specifically, as mentioned above, sequence data according to the tip position of the puncture needle is read from the transmit-and-receive memory 103.

In this manner, determining the first area 31 through detection of the tip portion of the puncture needle makes it possible to control the resolution of images and the frame rate with higher level as compared with a case where the first area 31 is fixedly determined. And as compared with a case where the first area 31 is set up through an operation of the handler by an operator, it is possible to save the operator's trouble thereby improving the operability.

It is acceptable that positional information of the tip of the puncture needle 30 is used for a designation of an ROI (region of interest) of the enlarged image. To practice the puncture technology, what is important is image information as to the tip vicinities of the puncture needle 30. Automatically determining an ROI (region of interest) of the enlarged image so as to always include the tip position of the puncture needle 30 makes it possible to always provide a display easy to see with an enlargement of the tip vicinities of the puncture needle 30, also while the puncture needle 30 is being introduced.

Figure 14:
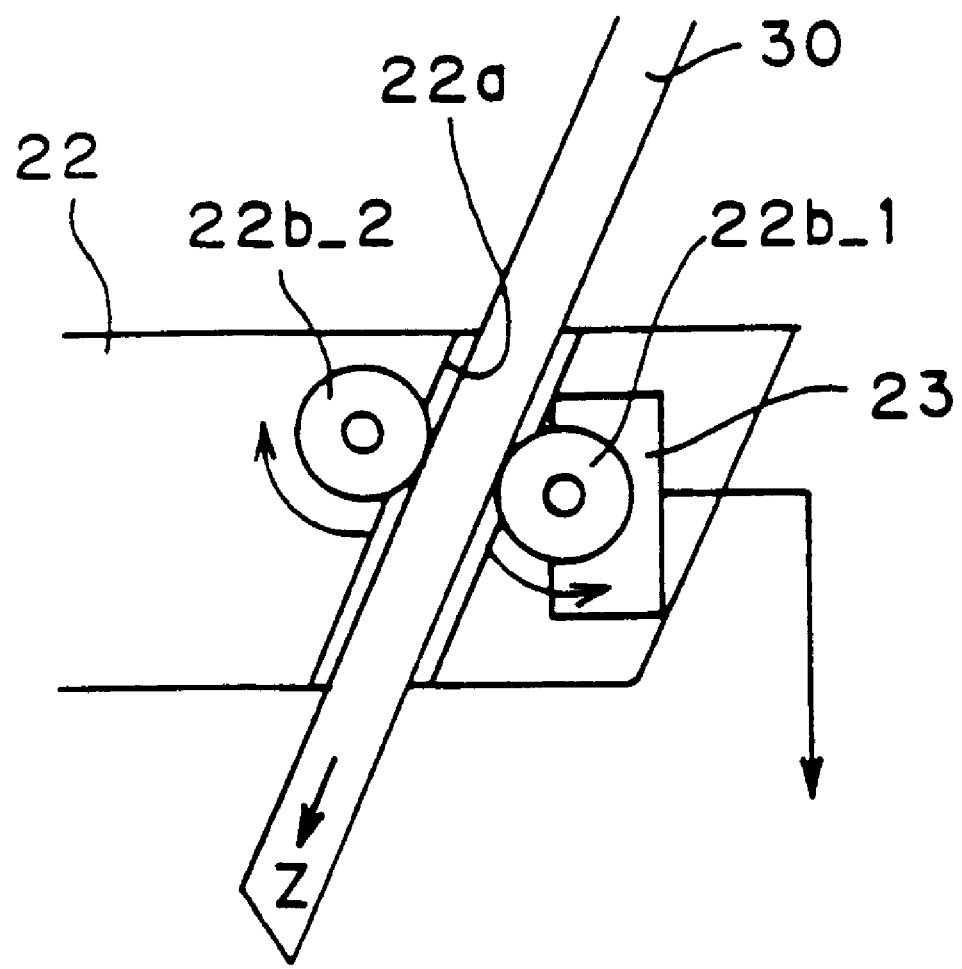
FIG. 14 is a typical sectional view of the internal structure of a portion encircled by a circle B shown in FIG. 7(A), of a guide member 22.

FIG. 14 is a typical sectional view of the internal structure of a portion encircled by a circle B shown in FIG. 7(A), of a guide member 22.

When the puncture needle 30 is inserted into the guide passage 22a for guiding the puncture needle 30, which is provided on the guide member 22, the puncture needle 30 is put between two roller 22b_1 and 22b_2 and introduced into the subject, while the two roller 22b_1 and 22b_2 rotate in arrow directions shown in FIG. 14, respectively. Coupled to one of the two roller 22b_1 and 22b_2, that is, the roller 22b_1 is a potentiometer 23 for measuring an amount of rotation of the roller 22b_1. Thus, the use of the potentiometer 23 makes it possible to identify how long the puncture needle 30 is introduced into the subject. An output of the potentiometer 23 is transferred via the control line 207, the control interface unit 204 and the CPU bus 901 to the control unit 100, and is used for an ROI designation in case of the designation of the first area and the enlargement of images shown in FIGS. 7(B) and 7(C), as a scheme taking the place of the scheme of directly detecting the tip position of the puncture needle 30, explained referring to FIGS. 12 and 13.

Figure 15A:
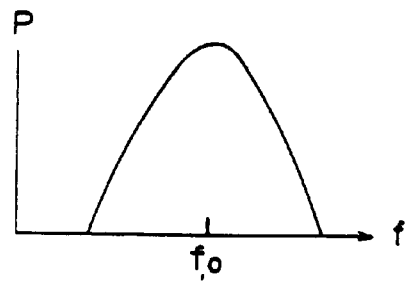
FIGS. 15(A) and 15(B) are views each showing a frequency distribution of ultrasonic beams transmitted from the ultrasonic transducers into the subject.
Figure 15B:
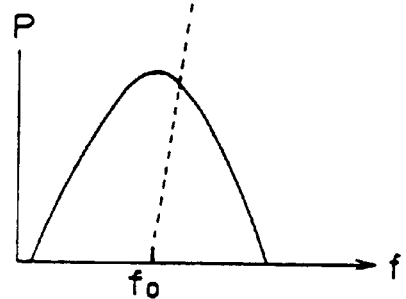

FIGS. 15(A) and 15(B) are views each showing a frequency distribution of ultrasonic beams transmitted from the ultrasonic transducers into the subject. In FIGS. 15(A) and 15(B), the axis of abscissas and the axis of ordinates stand for a frequency $\underline{f}$ of ultrasonic waves and a power P of the frequency, respectively.

In comparison of FIG. 15(A) with FIG. 15(B), it would be understood that the center frequency $f_o$ is set up to the higher frequency side in FIG. 15(A) than FIG. 15(B). A control of the center frequency $f_o$ is performed by means of controlling a pulse width and a repetitive period of the high voltage pulses to be applied to the ultrasonic transducers 211, as explained referring to FIGS. 4(A) and 4(B).

Here, in combination of the control of the center frequency $f_o$ with the scheme of detecting the tip position of the puncture needle 30, explained referring to FIGS. 12 and 13, when the tip of the puncture needle 30 is located at the relatively shallow position of the subject, there is performed transmit-and-receive of ultrasonic waves in which the center frequency $f_o$ is set up to the higher frequency side as shown in FIG. 15(A). As the tip of the puncture needle 30 is introduced deeply into the subject, there is performed transmit-and-receive of ultrasonic waves in which the center frequency $f_o$ is set up to the lower frequency side as shown in FIG. 15(B). While the use of the high frequency of ultrasonic waves makes it possible to obtain a high resolution of image, this involves an extreme attenuation, so that only the relatively shallower area of the subject can be simply observed. On the other hand, while the use of the low frequency of ultrasonic waves makes it possible to travel up to the deep area of the subject, it is worse in resolution as compared with the high frequency of ultrasonic waves. In view of the foregoing, according to the present embodiment, the use of ultrasonic waves having a frequency according to the position of the tip of the puncture needle 30 makes it possible to obtain a high resolution of image in accordance with the depth position of the tip of the puncture needle.

With respect to the tip position of the puncture needle and the frequency of ultrasonic waves to be used for transmit-and-receive, it is acceptable that the relationship between those is determined beforehand and stored in the transmit-and-receive memory 103, and the high voltage pulse to be applied to the ultrasonic transducers 211 is controlled on the basis of data read out from the transmit-and-receive memory 103 in accordance with the tip position of the puncture needle, alternatively it is acceptable that the relationship between the tip position of the puncture needle and the frequency of ultrasonic waves to be used for transmit-and-receive is provided beforehand in the form of the relation, and a frequency is determined by operation in accordance with information as to the tip position of the puncture needle, and then the high voltage pulse is controlled so that the ultrasonic waves having the frequency thus determined are transmitted and received.

While the embodiment has been described in such a manner that the scheme explained referring to FIGS. 12 and 13 is adopted to identify the position of the tip of the puncture needle, it is acceptable that the length of an insertion of the puncture needle 30 is measured as explained referring to FIG. 14, and the frequency of ultrasonic waves to be used for transmit-and-receive is altered in accordance with a relation with the length of the insertion thus measured.

Figure 16A:
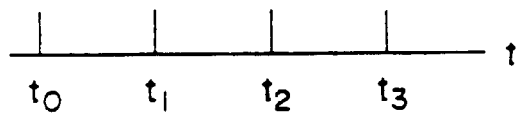
FIGS. 16(A) and 16(B) are views each showing a period of transmission of ultrasonic beams transmitted from the ultrasonic transducers into the subject.
Figure 16B:

FIGS. 16(A) and 16(B) are views each showing a period of transmission of ultrasonic beams transmitted from the ultrasonic transducers into the subject. In FIGS. 16(A) and 16(B), the axis of abscissas stands for a time axis $\underline{t}$ and it is assumed that ultrasonic beams are transmitted toward the inside of the subject at the respective times $t_o$, $t_1$, $t_2$, $t_3$, . . . .

Here, in combination of the transmission of the ultrasonic beams with the scheme of detecting the tip position of the puncture needle 30, explained referring to FIGS. 12 and 13, when the tip of the puncture needle 30 is located at the relatively shallow position of the subject, there is performed transmit-and-receive of ultrasonic beams at a short period as shown in FIG. 16(A). As the tip of the puncture needle 30 is introduced deeply into the subject, the intervals of the transmit-and-receive of ultrasonic beams are spread as shown in FIG. 16(B).

As mentioned above, ultrasonic waves slowly travel within the subject as compared with a velocity of a signal processing. Consequently, when the shallow area of the subject is to be observed, it is possible to narrow the period of the transmit-and-receive of ultrasonic beams as shown in FIG. 16(A). And there is a need to provide a longer period of the transmit-and-receive of ultrasonic beams, as it is intended to observe the deeper area within the subject.

Providing a short period of the transmit-and-receive of ultrasonic beams permits a lot of number of times of transmit-and-receive to be performed within the same time. This feature makes it possible to improve the resolution by providing the closer intervals of the scanning lines, and also to improve the tracking ability to a quick motion by increasing the frame rate.

In view of the foregoing, according to the present embodiment, ultrasonic beams are transmitted and received at the period according to the position of the tip of the puncture needle. This feature makes it possible to balance between the resolution and the frame rate at a possible high dimension in accordance with the depth position of the tip of the puncture needle.

It is acceptable that the relationship between the tip position of the puncture needle and the period of the transmit-and-receive of ultrasonic beams is kept being stored in the transmit-and-receive memory 103 shown in FIG. 12, and the transmit-receive unit 201 is controlled on the basis of data representative of the associated period of the transmit-and-receive read out from the transmit-and-receive memory 103 in accordance with the tip position of the puncture needle, alternatively it is acceptable that the relationship between the tip position of the puncture needle and the period of the transmit-and-receive of ultrasonic beams is provided beforehand in the form of the relation, and a period of the transmit-and-receive of ultrasonic beams is determined by operation in accordance with information as to the tip position of the puncture needle, and then the transmit-receive unit 201 is controlled on the basis of data thus obtained by the operation.

While the embodiment has been described in such a manner that the scheme explained referring to FIGS. 12 and 13 is adopted to identify the position of the tip of the puncture needle, it is acceptable that the length of an insertion of the puncture needle 30 is measured as explained referring to FIG. 14, and the period of the transmit-and-receive of ultrasonic beams is altered in accordance with a relation with the length of the insertion thus measured.

FIGS. 17(A) and 17(B) are illustrations each showing a beam configuration of ultrasonic beams. It is assumed that the transmitting ultrasonic beams and the received ultrasonic beam have the same beam configuration, and they will be explained without a particular distinction therebetween.

FIG. 17(A) shows an ultrasonic beam wherein a focus F, in which the beam is narrowed in diameter to the least, is formed at the relatively shallow site within the subject 1. FIG. 17(B) shows an ultrasonic beam wherein a focus F is formed at the relatively deep site within the subject 1. Since the beam diameter of the ultrasonic beam is fine in the vicinity of the focus F, it is possible to obtain a high resolution of image by the corresponding. Incidentally, the configuration of the ultrasonic beams can be controlled in accordance with the technique explained referring to FIG. 3, FIGS. 4(A)–4(B), FIG. 5, and FIGS. 6(A)–6(C).

Here, in combination of the configuration of the ultrasonic beams with the scheme of detecting the tip position of the puncture needle 30, explained referring to FIGS. 12 and 13, when the tip of the puncture needle 30 is located at the relatively shallow position of the subject, there is formed an ultrasonic beam having a focus at the shallow site. As the tip of the puncture needle 30 is introduced deeply into the subject, there is formed an ultrasonic beam having a focus at the deeper site.

As mentioned above, an alteration of the focus position of the ultrasonic beam is performed in accordance with the selected one from among a lot of scanning line data stored in the transmit-and-receive memory 103 shown in FIG. 1.

In this manner, according to the present embodiment, there is formed an ultrasonic beam having the focus at the site according to the tip position of the puncture needle 30. This feature makes it possible to obtain a high resolution of image suitable for the puncture technique.

While the embodiment has been described in such a manner that the scheme explained referring to FIGS. 12 and 13 is adopted to identify the position of the tip of the puncture needle, it is acceptable that the scheme of measuring the length of an insertion of the puncture needle 30, as explained referring to FIG. 14, is adopted and the site of the focus of the ultrasonic beam is altered in accordance with a relation with the length of the insertion measured.

While there has been described technologies of altering a frequency of ultrasonic waves, a period of transmit-and-receive of ultrasonic beams and a focus position of an ultrasonic beam in accordance with the position of the tip of the puncture needle 30 or the length of the insertion of the puncture needle 30, in conjunction with FIGS. 15(A)–15(B), FIGS. 16(A)–16(B) and FIGS. 17(A)–17(B), respectively, it is acceptable that those are implemented independently of one another, alternatively a plurality of ones of those technologies are selectively combined with each other and implemented in their combination simultaneously. Further, it is acceptable that those technologies are selectively combined with the various types of technologies previously explained, for example, an alteration of the density of the scanning line, setting up of the enlarged area, etc., and then implemented.

Figure 18:
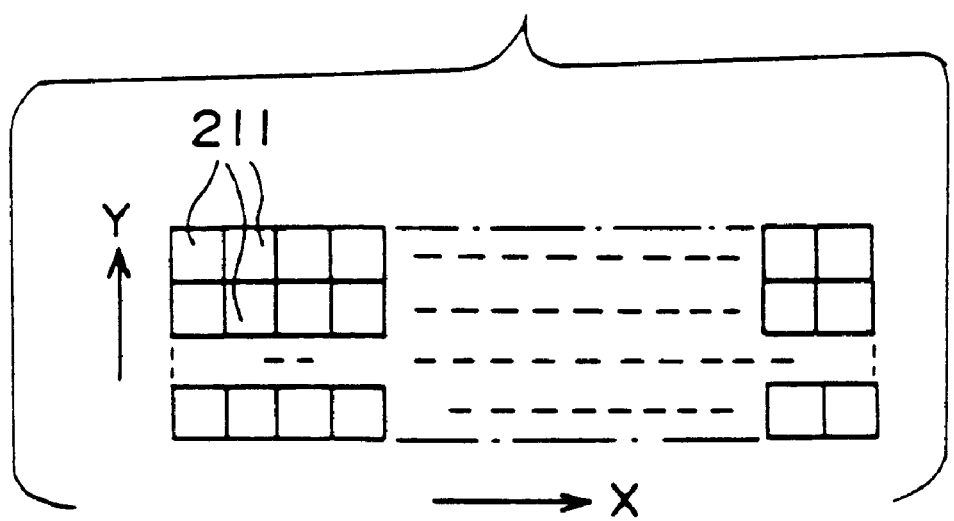
FIG. 18 is a view showing a two-dimensional arrangement of ultrasonic transducers.

FIG. 18 is a view showing a two-dimensional arrangement of ultrasonic transducers.

According to the above explanation, the ultrasonic transducers 211 provided on the ultrasonic probe 20 are essentially arranged as a circular arc on a line, while it is not particularly restricted. But it is acceptable that the ultrasonic transducers 211 are arranged on a two-dimensional basis. FIG. 18 shows ultrasonic transducers 211 arranged on a two-dimensional basis in an X-direction and a Y-direction.

Figure 19:
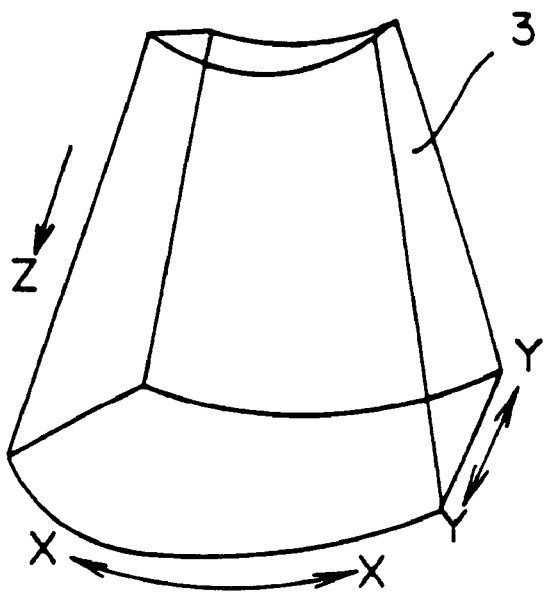
FIG. 19 is a view showing a scanning area associated with the scan using an ultrasonic probe having a two-dimensional arrangement of ultrasonic transducers.

FIG. 19 is a view showing a scanning area associated with the scan using an ultrasonic probe having a two-dimensional arrangement of ultrasonic transducers as shown in FIG. 18.

In this case, the inside of the subject is scanned in not only an X—X direction, but also a Y—Y direction, so that a three-dimensional scanning area 3 as shown in FIG. 19 is obtained.

Figure 20:
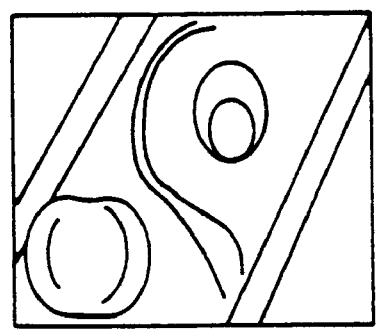
FIG. 20 is a view representative of a three-dimensional image in which a depth is expressed.

FIG. 20 is a view representative of a three-dimensional image in which a depth is expressed.

In association with that a three-dimensional scanning area 3 as shown in FIG. 19 is obtained, a three-dimensional tomographic image within the subject can be displayed.

When the puncture needle is introduced into the subject, it happens that the puncture needle does not always travel along a predetermined passage, but makes a turn owing to a difference between tissues in toughness at the boundary of tissues within the subject, and travels along a path out of the predetermined passage. In addition, it happens that the path out of the predetermined passage is concerned with a Y-direction not restricted to an X-Y plane shown in FIG. 19. In such a case, simply displaying the two-dimensional tomographic image may invite such a result that the tip of the puncture needle is out of the displayed image and thus an operator cannot sufficiently observe the tip of the puncture needle. For these reasons, there is used the ultrasonic probe in which the ultrasonic transducers 211 are arranged on a two-dimensional basis, as shown in FIG. 18, so that the three-dimensional scanning area 3 as shown in FIG. 19 is obtained, and the three-dimensional image as shown in FIG. 20 is displayed. This feature makes it possible to exactly observe the tip of the puncture needle, even if the tip of the puncture needle makes a turn in any direction, so as to take a care of not injuring other tissues.

Incidentally, since it takes a lot of time for a generation of a three-dimensional image, it is preferable that the three-dimensional image is produced only on the vicinity of tip of the puncture needle. As a technology of restricting the image generating area to the vicinity of the of tip of the puncture needle, it is possible to adopt the scheme of the ROI designation for enlarged images, as previously explained, as it is.

Further, the various technologies previously explained are applicable also to the cases of a generation of three-dimensional images explained referring to the FIG. 19 to FIG. 20, in their present form, as far as they are not in conflict with their nature.

Incidentally, according to the above-mentioned embodiments in its entirety, while there is adopted an ultrasonic probe in which a plurality of ultrasonic transducers are arranged, it is to be noted that there is also known such a technology that regarding the ultrasonic diagnostic apparatus, instead of providing a plurality of ultrasonic transducers, a single ultrasonic transducer having an acoustic lens on a front is provided, and while the ultrasonic transducer is mechanically moved on a one-dimensional basis or a two-dimensional basis, ultrasonic waves are transmitted and received thereby scanning the inside of the subject with the ultrasonic waves. Also in the present invention, it is acceptable that such a technology is adopted to implement various sorts of technologies as previously explained as far as they are not conflict with their nature. As a case where it is conflict with its nature, it will be considered that, for example, in the event that this technology is adopted, the acoustic lens is fixed in its focus and then it is difficult to implement such a scheme that a focus is varied in accordance with a site of the tip of the puncture needle.

As mentioned above, according to the ultrasonic diagnostic apparatus of the present invention, it is possible to produce images suitable for the puncture technique.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said transmit-receive unit has a first transmit-receive mode in which said scanning area is scanned with a predetermined scanning density, and a second transmit-receive mode in which, of said scanning area, a predetermined first area including a part or a whole of a passage of the puncture needle is scanned with a scanning density higher than that of a second area, excepting the first area, of said scanning area, and said ultrasonic probe has a sensor for measuring a length of a portion of a tip end of the puncture needle passing through said guide member, and said transmit-receive unit sets up the first area in accordance with the length measured by said sensor.

2. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said transmit-receive unit has a first transmit-receive mode in which said scanning area is scanned with a predetermined scanning density, and a second transmit-receive mode in which, of said scanning area, a predetermined first area including a part or a whole of a passage of the puncture needle is scanned with a scanning density higher than that of the first transmit-receive mode, wherein said ultrasonic probe has a sensor for measuring a length of a portion of a tip end of the puncture needle passing through said guide member, and said transmit-receive unit sets up the first area in accordance with the length measured by said sensor.

3. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said transmit-receive unit has a first transmit-receive mode in which said scanning area is scanned with a predetermined scanning density, and a second transmit-receive mode in which, of said scanning area, a predetermined first area including a part or a whole of a passage of the puncture needle is scanned with a scanning density higher than that of a second area, excepting the first area, of said scanning area, wherein said image producing unit has a first image producing mode for producing a first image representative of the whole area of said scanning area, and a second image producing mode for producing a second image representative of an enlarged area consisting of a partial area including at least part of the passage of the puncture needle, of said scanning area, or an enlarged area consisting of the whole area of said scanning area, a size per unit area within the subject of the second image being enlarged more than the first image, and wherein said ultrasonic probe has a sensor for measuring a length of a portion of a tip end of the puncture needle passing through said guide member, and said image producing unit sets up the enlarged area in accordance with the length measured by said sensor.

4. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said transmit-receive unit has a first transmit-receive mode in which said scanning area is scanned with a predetermined scanning density, and a second transmit-receive mode in which, of said scanning area, a predetermined first area including a part or a whole of a passage of the puncture needle is scanned with a scanning density higher than that of the first transmit-receive mode, wherein said image producing unit has a first image producing mode for producing a first image representative of the whole area of said scanning area, and a second image producing mode for producing a second image representative of an enlarged area consisting of a partial area including at least part of the passage of the puncture needle, of said scanning area, or an enlarged area consisting of the whole area of said scanning area, a size per unit area within the subject of the second image being enlarged more than the first image, and wherein said ultrasonic probe has a sensor for measuring a length of a portion of a tip end of the puncture needle passing through said guide member, and said image producing unit sets up the enlarged area in accordance with the length measured by said sensor.

5. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said ultrasonic probe has a sensor for measuring a length of a portion of a tip end of the puncture needle passing through said guide member, and said transmit-receive unit drives said at least one ultrasonic transducer so as to form the ultrasonic beam having a frequency according to a length measured by said sensor.

6. An ultrasonic diagnostic apparatus according to claim 5, wherein transmission and reception of ultrasonic beams along a plurality of scanning lines arranged on a three-dimensional basis extending to the inside of the subject are repeatedly performed to scan the inside of the subject, and an image on a three-dimensional scanning area defined by the plurality of scanning lines is produced in accordance with a received signal obtained by the scanning.

7. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said ultrasonic probe has a sensor for measuring a length of a portion of a tip end of the puncture needle passing through said guide member, and said transmit-receive unit drives said at least one ultrasonic transducer so as to sequentially form ultrasonic beams with a period according to a length measured by said sensor.

8. An ultrasonic diagnostic apparatus according to claim 7, wherein transmission and reception of ultrasonic beams along a plurality of scanning lines arranged on a three-dimensional basis extending to the inside of the subject are repeatedly performed to scan the inside of the subject, and an image on a three-dimensional scanning area defined by the plurality of scanning lines is produced in accordance with a received signal obtained by the scanning.

9. An ultrasonic diagnostic apparatus in which transmission and reception of ultrasonic beams along a plurality of scanning lines extending to an inside of a subject are repeatedly performed to scan the inside of the subject, and an image on a scanning area defined by the plurality of scanning lines is produced in accordance with a received signal obtained by the scanning, said ultrasonic diagnostic apparatus comprising:

an ultrasonic probe having a main frame having at least one ultrasonic transducer put to the subject to perform transmission of ultrasonic waves into the subject and reception of ultrasonic waves reflected within the subject, and a guide member for guiding a puncture needle introduced into the subject;

a transmit-receive unit for driving said at least one ultrasonic transducer to sequentially generate ultrasonic waves traveling along the plurality of scanning lines, and deriving received signals by receiving by said at least one ultrasonic transducer ultrasonic waves reflected within the subject and returned to said at least one ultrasonic transducer; and an image producing unit for producing an image based on the received signal, wherein said ultrasonic probe has a sensor for measuring a length of a portion of a tip end of the puncture needle passing through said guide member, and said transmit-receive unit drives said at least one ultrasonic transducer so as to vary a focal distance of the ultrasonic beam in accordance with a length measured by said sensor.

10. An ultrasonic diagnostic apparatus according to claim 9, wherein transmission and reception of ultrasonic beams along a plurality of scanning lines arranged on a three-dimensional basis extending to the inside of the subject are repeatedly performed to scan the inside of the subject, and an image on a three-dimensional scanning area defined by the plurality of scanning lines is produced in accordance with a received signal obtained by the scanning.

11. An ultrasonic diagnostic apparatus to repeatedly scan inside of a subject, said ultrasonic diagnostic apparatus comprising:

an ultrasonic probe to transmit and receive ultrasonic waves inside the subject and produce a signal in response to received ultrasonic waves;

an image producing unit to produce an image based on the signal produced from said ultrasonic probe; and an oscillation mechanism for vibrating a tip of a puncture needle, wherein a predetermined first area including a part or a whole of a passage of the puncture needle is scanned with a scanning density higher than that of a second area, excepting the first area, and said ultrasonic probe has a sensor for measuring a length of a portion of a tip end of the puncture needle passing through said guide member, and sets up the first area in accordance with the length measured by said sensor.

12. An ultrasonic diagnostic apparatus, comprising:

an ultrasonic probe to transmit and receive ultrasonic waves; and an oscillation mechanism to vibrate a tip of a puncture needle within a subject, wherein a first area about the puncture needle is scanned with higher density than a second adjacent area, and said ultrasonic probe has a sensor for measuring a length of a portion of a tip end of the puncture needle passing through said guide member, and sets up the first area in accordance with the length measured by said sensor.

* * * * *

UNITED STATES PATENT AND TRADEMARK OFFICE
CERTIFICATE OF CORRECTION

PATENT NO.: 6,146,329
DATED : November 14, 2000
INVENTOR(S): Hayakawa

It is certified that an error appears in the above-identified patent and that said Letters Patent is hereby corrected as shown below:

[57] ABSTRACT,
 The last sentence of the Abstract should be deleted.

Signed and Sealed this

First Day of May, 2001

Attest:

NICHOLAS P. GODICI

Attesting Officer *Acting Director of the United States Patent and Trademark Office*